US011858877B2

(12) United States Patent
Camacho et al.

(10) Patent No.: US 11,858,877 B2
(45) Date of Patent: Jan. 2, 2024

(54) SMALL MOLECULES THAT SPECIFICALLY INHIBIT TNF-INDUCED NF-KB INFLAMMATION PATHWAY

(71) Applicant: UNIVERSITY OF PITTSBURGH—OF THE COMMONWEALTH SYSTEM OF HIGHER EDUCATION, Pittsburgh, PA (US)

(72) Inventors: Carlos Jaime Camacho, Pittsburgh, PA (US); Robin E. C. Lee, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 954 days.

(21) Appl. No.: 16/799,130

(22) Filed: Feb. 24, 2020

(65) Prior Publication Data

US 2020/0325098 A1    Oct. 15, 2020

Related U.S. Application Data

(60) Provisional application No. 62/809,459, filed on Feb. 22, 2019.

(51) Int. Cl.
    *C07C 233/08*    (2006.01)
    *A61K 31/00*    (2006.01)

(52) U.S. Cl.
    CPC ............ *C07C 233/08* (2013.01); *A61K 31/00* (2013.01)

(58) Field of Classification Search
    CPC ..... C07C 233/08; C07C 317/48; A61K 31/00; A61K 31/245; A61K 31/395
    See application file for complete search history.

(56) References Cited

PUBLICATIONS

Banker (Modern Pharmaceutics) (Banker, G.S. et al, "Modern Pharmaceutics, 3ed.", Marcel Dekker, New York, 1996.*
Wolff, Manfred E. "Burger's Medicinal Chemistry, 5ed, Part I", John Wiley & Sons, 1995, pp. 975-977.*
Baumgartner, et al., "Choosing the Optimal Rigid Receptor for Docking and Scoring in the CSAR 2013/2014 Experiment," *J Chem. Inf. Model*, vol. 56, pp. 1004-1012 (2016).
Beck, et al., "Crosstalk in Inflammation: The Interplay of Glucocorticoid Receptor-based Mechanisms and Kinases and Phosphatases," *Endocr Rev.*, vol. 30, pp. 830-882 (2009).
Behar, et al., "The Dynamics of Signaling as a Pharmacological Target," *Cell* 155, pp. 448-461 (2013).
Berman et al., "The Protein Data Bank," *Nucleic Acids Res.*, vol. 28, pp. 235-242 (Jan. 2000).
Chee-Kwee Ea, et al., "Activation of IKK by TNFa Requires Site-Specific Ubiquitination of RIP1 and Polyubiquitin Binding by NEMO," *Molecular Celli*, vol. 22, pp. 245-257 (Apr. 2006).

(Continued)

*Primary Examiner* — Deborah D Carr
(74) *Attorney, Agent, or Firm* — FOLEY & LARDNER LLP

(57) ABSTRACT

Provided herein are small molecules that specifically inhibit TNF-induced nuclear factor kB (NF-kB) inflammation pathway. Also provided are methods of screening compounds to identify molecules that specifically inhibit a TNF-induced NF-kB inflammation pathway, methods of inhibiting TNF-induced NF-kB inflammation pathway, and methods of preventing formation of mature TNFR1 complex.

21 Claims, 20 Drawing Sheets

Specification includes a Sequence Listing.

(56) References Cited

PUBLICATIONS

Chatr-aryamontri, et al., "The BioGRID Interaaction Database: 2015 Update," *Nucleic Acids Research*, vol. 43, pp. 470-478 (Nov. 2014).

Clark, et al., "Molecular control of the NEMO family of ubiquitin-binding proteins," Nature Reviews Molecular Cell Biology, vol. 14, pp. 673-685 (Aug. 2013).

Dave, et al, "Amelioration of Chronic Murine Colitis by Peptide-Mediated Transduction of the I κb Kinase Inhibitor NEMO Binding Domain Peptide," *J Immunol* 179, pp. 7852-7859 (2007).

DiDonato et al., "NF-κB and the Link Between Inflammation and Cancer," *Immunol. Rev.*, 246, pp. 379-400 (2012).

Haas, et al., "Recruitment of the Linear Ubiquitin Chain Assembly Complex Stabilizes the TNF-R1 Signaling Complex and Is Required for TNF-Mediated Gene Induction," *Mol. Cell* 36, pp. 831-844 (2009).

Hayden, et al., "Shared Principles in NF-κB Signaling," *Cell* 132, pp. 344-362 (2008).

Hayden, et al., "Signaling to NF-κB," *Genes Dev* 18, pp. 2195-2224 (2004).

Hsu, et al., "TNF-Dependent Recruitment of the Protein Kinase RIP to the TNF Receptor-1 Signaling Complex," Immunity 4, pp. 387-396 (1996).

Ikeda, et al., "Sharpin forms a linear ubiquitin ligase complex regulating NF-κB activity and apoptosis," Nature 471, pp. 637-641 (2011).

Kasibhatla, et al., DNA Damaging Agents Induce Expression of Fas Ligand and Subsequent Apoptosis in T Lymphocytes via the Activation of NF-κB and AP-1, *Mol Cell* 1, pp. 543-551 (1998).

Keenan, et al., "The Library of Integrated Network-based Cellular Signatures (LINCS) NIH Program: System-level Cataloging of Human Cells Response to Perturbations," *Cell Syst.*, vol. 6, No. 1, pp. 13-24 (Jan. 2018).

Koes, et al., "Lessons Learned in Empirical Scoring with smina from the CSAR 2011 Benchmarking Exercise," *J Chem Inf Model* 53, pp. 1893-1904 (2013).

Kozakov, et al., "The FTMap Family of Web Servers for Determining and Characterizing Ligand Binding Hot Spots of Proteins," *Nature protocols* 10, pp. 733-755 (2015).

Kulathu, et al., "Two-sided Ubiquitin Binding Explains Specificity of the TAB2 NZF Domain," Nat Struct Mol Biol 16, pp. 1328-1330 (2009).

Kuntz et al., "The Maximal Affinity of Ligands," *Proc. Natl. Acad. Sci.*, vol. 96, pp. 9997-10002 (1999).

Lawrence, "The Nuclear Factor NF- κB Pathway in Inflammation," T. *Cold Spring Harb Perspect Biol* 1, 11 pages (2009).

Lee, et al., "NF-κB signalling and cell fate decisions in response to a short pulse of tumour necrosis factor," Sci, Reports 6, 12 pages (2016).

Lee, et al., "Fold Change of Nuclear NF-κB Determines TNF-Induced Transcription in Single Cells," *Mol Cell* 53, pp. 867-879 (2014).

Lewis, et al., "Distinct Role of Macrophages in Different Tumor Microenvironments," *Cancer Research*, vol. 66, pp. 605-612 (2006).

Li, et al., "NF-κB Regulation in the Immune System," *Nat Rev Immunol* 2, pp. 725-734 (2002).

Li et al., Severe Liver Degeneration in Mice Lacking the IkB Kinase 2 Gene, *Science*, vol. 284, pp. 321-325 (Apr. 1999).

Marx, Inflammation and Cancer: The Link Grows Stronger, Science 306, 966-968 (2004) [1$^{st}$ page Abstract].

Mullard, "Protein—protein interaction inhibitors get into the groove: drug developers are getting closer to tapping an unmined gold reserve of protein—protein interaction targets," A., *Nat. Rev. Drug Discov.*, 11, pp. 173-175 (2012).

Pabon, et al., "Predicting Protein Targets for Drug-Like Compounds using Transcriptomics," *PLoS Comput. Biol.*, vol. 14, No. 12, 24 pages (Dec. 2018).

Pahl, "Activators and target genes of Rel/NF-κB transcription factors," *Oncogene* 18, pp. 6853-6866 (1999).

Park, et al., "A Novel Mechanism of TRAF Signaling Revealed by Structural and Functional Analyses of the TRADD-TRAF2 Interaction," *Cell* 101, pp. 777-787 (2000).

Park, et al., "Structural Basis for Self-Association and Receptor Recognition of Human TRAF2," *Nature* 398, pp. 533-538 (1999).

Sahni, et al., "Edgotype: the link between genotype and phenotype," Curr. Opin. Genet. Dev., vol. 23, pp. 649-657 (2013).

Sahni, et al., "Widespread Macromolecular Interaction Perturbations in Human Genetic Disorders," *Cell*, vol. 161, No. 3, pp. 647-660 (Apr. 2015).

Schottenfeld, et al., "Chronic Inflammation: A Common and Important Factor in the Pathogeneiss of Neoplasia," *CA Cancer J Clin* 56, pp. 69-83 (2006).

Shibata, et al., "Cutting Edge: The IkB Kinase (IKK) Inhibitor, NEMO-Binding Domain Peptide, Blocks Inflammatory Injury in Murine Colitis," *J Immunol* 179, pp. 2681-2685 (2007).

Staudt, et al., "Oncogenic Activation of NF-κB," *Cold Spring Harb Perspect Biol* 2, 31 pages (2010).

Tak, et al., "NF-κB: A Key Role in Inflammatory Diseases," G. S. *J Clin Invest* 107, pp. 7-11 (2001).

Tarantino, et al., "TNF and IL-1 exhibit distinct ubiquitin requirements for inducing NEMO-IKK supramolecular structures," *J Cell Biol* 204, pp. 231-245 (2014).

Wajant, et al., "TNFR1-induced activation of the classical NF-jB pathway," *FEBS J* 278, pp. 862-876 (2011).

Wong, et al., NF-κB-Chromatin Interactions Drive Diverse Phenotypes by Modulating Transcriptional Noise, *Cell Rep* 22, pp. 585-599 (2018).

Ye et al., "Optimal strategies for virtual screening of induced-fit and flexible target in the 2015 D3R Grand Challenge," *J. Comput. Aided Mol. Des.*, vol. 30, pp. 695-706 (Sep. 2016).

Zarnegar, et al., "Activation of noncanonical NF-κB requires coordinated assembly of a regulatory complex of the adaptors cIAP1, cIAP2, TRAF2, TRAF3 and the kinase NIK," *Nat Immunol* 9, pp. 1371-1378 (2008).

Zhang, et al., "NF-κB Dynamics Discriminate between TNF Doses in Single Cells," *Cell Syst* 5, pp. 638-645 ( 2017).

\* cited by examiner

SEQUENCE LISTING

<160> NUMBER OF SEQ ID NOS: 15

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Ser Gly Gly Gly Ser Gly Gly Gly Ser Gly
1               5                   10

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gggcgaattg ggcccgacgt cgtttcaccg tgttagccag g                    41

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cacatcctta cccagcaga                                             19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agagtctcct ctggggaagc                                            20

<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccgccatggc ggccgggagc atgcgacgtc agtctaggaa agaactcccc agtc      54

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tctgctgggt aaggatgtg                                                    19

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gctcttgatt ctcctccagg cag                                               23

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
caccgctcgt ctgtagtgca cgccg                                             25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aaaccggcgt gcactacaga cgagc                                             25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
caccgagagg cggaaatgcg ccgcc                                             25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aaaccgcggc gcatttccgc ctctc                                             25

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
caccggcagc agatcaggac gtac                                              24

```
<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaacgtacgt cctgatctgc tgcc                                          24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
caccgctgca ccatctcaca cagt                                          24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aaacactgtg tgagatggtg cagc                                          24
```

SMALL MOLECULES THAT SPECIFICALLY INHIBIT TNF-INDUCED NF-KB INFLAMMATION PATHWAY

CROSS-REFERENCE TO RELATED APPLICATIONS

This application claims the benefit of U.S. Provisional Patent Application No. 62/809,459, filed Feb. 22, 2019, which is incorporated by reference herein in its entirety.

FEDERAL FUNDING STATEMENT

This invention was made with government support under GM097082 and GM119462 awarded by the NIH and NSF grant GRFP1247842. The government has certain rights in the invention.

SEQUENCE LISTING

The instant application contains a Sequence Listing which has been filed electronically in ASCII format and is hereby incorporated by reference in its entirety. Said ASCII copy, created on Jun. 4, 2020, is named 076333-0937_SL.txt and is 3,853 bytes in size.

BACKGROUND

Small-molecules are a promising class of protein-protein interactions (PPI) inhibitors to perturb signaling networks in vivo, but they are technically difficult to identify and assess. Instead, many PPI inhibitors are derived from competitive peptides with challenging cell permeability and pharmacokinetic properties (Mullard, A., *Nat. Rev. Drug Discov.*, 11:173-175 (2012)).

Tumor Necrosis Factor (TNF)-induced NF-kB signaling is an example of a tightly regulated and therapeutically relevant pathway that has resisted target-centric drug discovery.

Chemicals that modulate inflammation-dependent IkB-kinase (IKK) and NF-kB signals are of considerable therapeutic interest. The complexity of the pathway and the difficulty of modulating specific protein-protein interactions in vivo exacerbates the challenges of drugging this pathway in the cell (DiDonato et al., Immunol. Rev., 246: 379-400 (2012)). Not surprisingly, there are no clinically approved small-molecule inhibitors of NF-kB pathway components.

Therefore, a need exists to identify new small-molecule inhibitors of NF-kB pathway components.

SUMMARY

The present disclosure is directed to new small-molecule inhibitors of NF-kB pathway components and methods of using the same.

One aspect provides compounds represented by formula (I):

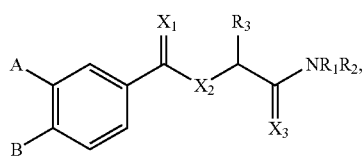

or a salt, solvate, hydrate or prodrug thereof, wherein A is an azinic acid; B is an alkyl sulfonyl; $X_1$ and $X_3$ are independently selected from O, NOH, NO-alkyl, $CF_3$, and $C(CN)_2$; $X_2$ is selected from O, NH, and NF; $R_1$ is H or alkyl; $R_2$ is an optionally substituted alkyl or cycloalkyl, or $R_1$ and $R_2$ together form an optionally substituted 5- or 6-membered heterocycle; and $R_3$ is selected from H, F, and an optionally substituted alkyl, where the compound of formula (I) is not:

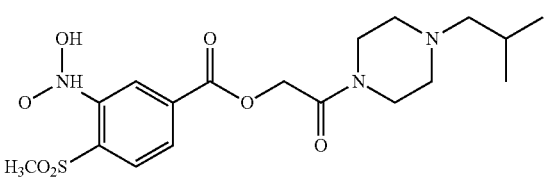

or

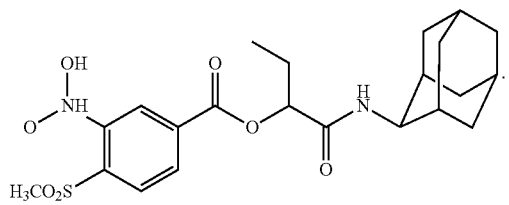

In some embodiments, $-NR_1R_2$ is represented by:

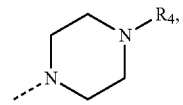

wherein $R_4$ is an optionally substituted alkyl, alkene, alkyne, or $-COOR_5$, where $R_5$ is an optionally substituted alkyl or cycloalkyl. In some embodiments, $X_1$, $X_2$ and $X_3$ are O. In some embodiments, $R_3$ is H. In some embodiments, $R_2$ is a cyclopentyl or cyclohexyl.

In other aspects, $X_1$, $X_2$ and $X_3$ can be O. In yet other aspects, $R_3$ is H. In other aspects, $R_2$ is a cyclopentyl or cyclohexyl.

Also described is a pharmaceutical composition comprising a compound disclosed herein and at least one pharmaceutically acceptable carrier. In some embodiments, the pharmaceutical composition is suitable for administration to a human. For example, the pharmaceutical composition can be formulated into a dosage form: (a) selected from the group consisting of liquid dispersions, gels, aerosols, lyophilized formulations, tablets, and capsules; (b) selected from the group consisting of controlled release formulations, fast melt formulations, delayed release formulations, extended release formulations, pulsatile release formulations, and mixed immediate release and controlled release formulations; or (c) any combination of (a) and (b). In addition, the pharmaceutical composition can be formulated for administration selected from the group consisting of oral, pulmonary, rectal, colonic, parenteral, intracisternal, intravaginal, intraperitoneal, intravenous, subcutaneous, intramuscular, nebulization, inhalation, ocular, otic, local, buccal, nasal, and topical administration.

Other aspects include a method of preventing formation of mature TNFR1 complex, comprising contacting a cell with a compound of formula (I):

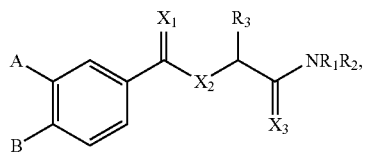

or a salt, solvate, hydrate or prodrug thereof, wherein A is an azinic acid; B is an alkyl sulfonyl; $X_1$ and $X_3$ are independently selected from O, NOH, NO-alkyl, $CF_3$, and $C(CN)_2$; $X_2$ is selected from O, NH, and NF; $R_1$ is H or alkyl; $R_2$ is an optionally substituted alkyl or cycloalkyl, or $R_1$ and $R_2$ together form an optionally substituted 5- or 6-membered heterocycle.

In one aspect of the method, the cell is a human cell. In addition, the method can be in vivo or in vitro. Further, the contacting can be in vivo in a subject suffering from a disease caused by blockade of TNF-induced signaling or in a subject suffering from a disease caused by inflammation-associated cancers that are potentiated by TNF-induces NFkB signaling. In other aspects of the method, the disease can be selected from the group consisting of rheumatoid arthritis, ankylosing spondylitis, inflammatory bowel disease, and psoriasis. Alternatively, the cancer can be selected from the group consisting of aggressive diffuse large B-cell lymphoma, metastatic carcinomas, tumors of the colon, tumors of the lung, tumors of the pancreas, and tumors of the brain.

Other aspects include a method of inhibiting a TNF-induced nuclear factor kB (NF-kB) inflammation pathway, comprising contacting a cell with a compound of formula (I):

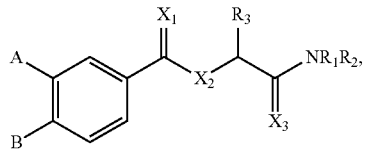

or a salt, solvate, hydrate or prodrug thereof, wherein A is an azinic acid; B is an alkyl sulfonyl; $X_1$ and $X_3$ are independently selected from O, NOH, NO-alkyl, $CF_3$, and $C(CN)_2$; $X_2$ is selected from O, NH, and NF; $R_1$ is H or alkyl; $R_2$ is an optionally substituted alkyl or cycloalkyl, or $R_1$ and $R_2$ together form an optionally substituted 5- or 6-membered heterocycle.

In one aspect of the method, the cell is a human cell. In addition, the method can be in vivo or in vitro. Further, the contacting can be in vivo in a subject suffering from a disease caused by blockade of TNF-induced signaling or in a subject suffering from a disease caused by inflammation-associated cancers that are potentiated by TNF-induces NFkB signaling. In other aspects of the method, the disease can be selected from the group consisting of rheumatoid arthritis, ankylosing spondylitis, inflammatory bowel disease, and psoriasis. Alternatively, the cancer can be selected from the group consisting of aggressive diffuse large B-cell lymphoma, metastatic carcinomas, tumors of the colon, tumors of the lung, tumors of the pancreas, and tumors of the brain.

Finally, the disclosure encompasses a method of treating a subject suffering from a disease caused by blockade of TNF-induced signaling, comprising administering to the subject in need thereof a pharmaceutically effective amount of the compound of Formula (I). In addition, the disease caused by blockade of TNF-induced signaling can be selected from the group consisting of rheumatoid arthritis, ankylosing spondylitis, inflammatory bowel disease, and psoriasis.

Both the foregoing summary of the invention and the following brief description of the drawings and detailed description of the invention are exemplary and explanatory and are intended to provide further details of the invention as claimed. Other objects, advantages, and novel features will be readily apparent to those skilled in the art from the following detailed description of the invention.

BRIEF DESCRIPTION OF DRAWINGS

FIG. 1(a) Schematic of the mature TNFR1 complex, a cytoplasmic multi-protein complex that assembles following ligation of TNF to TNFR1. The color for each protein species in the complex is the average Pearson correlation between gene expression profiles for the species' genetic knockdown and the transcriptional response to compounds 2 and 3. FIG. 1(b) Correlation between transcriptomic perturbations by compounds 1, 2, and 3 and the knockdown of genes functionally involved in NF-kB according to the KEGG PATHWAY Database. FIG. 1(c) Unbiased molecular docking predicts binding of compounds 2 (yellow) and 3 (magenta) to the TRADD-binding interface of TRAF2. Hydrogen bonds with key TRAF2 interface residues are indicated by dotted lines.

FIG. 3(a) Time-lapse images of FP-RelA expressed from its endogenous gene locus in U2OS cells exposed to TNF. The nuclear subcellular compartment is indicated with a broken yellow line. Scale bar 20 μm for all. FIG. 3(b) Single cell time courses of nuclear FP-RelA measure the change in the nuclear abundance of NF-kB in response to the indicated conditions. Red numbers indicate the number of single cell trajectories in each condition. FIG. 3(c) Descriptors used to quantify single cell responses. AUC, Max, and $t_{max}$, respectively, describe the area under the curve, the maximum, and the time of maximal nuclear FP-RelA fluorescence. $Rate_{in}$ and $Rate_{out}$ describe the maximal rate of nuclear entry and exit. FIG. 3(d) Box (first and third quartile) and whisker (1.5 times interquartile range) plots showing the condition-specific variation for descriptors of nuclear FP-RelA localization. Red bars indicate the median; **$p \ll 10^{-6}$, based on permutation test (FIG. 12).

FIG. 4(a) Single-cell time courses of nuclear FP-RelA quantified in cells exposed to 100 ng/mL IL1 in addition to either DMSO (top), 10 µM Compound 2 (middle), or 10 µM Compound 3 (bottom). Red numbers indicate the number of single-cell trajectories for each condition. FIG. 4(b) Descriptors for the 'area under the fold change curve' (top) and the 'maximum fold change of nuclear FP-RelA (bottom) for indicated conditions measured from FIG. 4(a) do not show significant changes based on permutation tests (FIG. 15).

FIG. 5(a) Time-lapse images of FP-IKK expressed from its endogenous gene locus in U2OS cells exposed to TNF. FIG. 5(b) Single-cell time courses for the number of FP-IKK puncta in cells stimulated with the indicated conditions. In all TNF conditions, a concentration of 100 ng/mL was used.

FIG. 9(a) Normalized melt curve of full length TRAF2 was recorded in the presence of DMSO or indicated concentrations of compound 1 (orange lines). FIG. 9(b) Melting temperature of TRAF2 in the present of compound 1 is not significantly altered in replicate experiments.

FIG. 10(a) Western blot of RelA in lysates from parental U2OS cells (P) and U2OS cells that were modified using CRISPR to express EGFP-RelA. The molecular weight of the dominant FP-RelA band in the CRISPR-modified cell line is shifted upward by 32 kDa, consistent with the expected molecular weight of the EGFP fusion protein. The presence of the wild type RelA band in the CRISPR-modified cell line suggests that only one allele of the RelA-encoding gene integrated the EGFP-encoding sequence. FIG. 10(b) Subcellular localization of RelA from fixed-cell immunofluorescence images of parental U2OS (left) and FP-RelA quantified from live cells using the CRISPR-modified cell line (right) exposed to 10 ng/mL TNF show similar temporal dynamics. Average of single cells (dark line) and standard deviation (light line) are shown.

FIG. 13(a) Single cell time courses measure the change in nuclear abundance of FP-RelA in cells exposed to 10 ng/mL TNF after pre-incubation with Compound 1. Red number indicates the number of single-cell trajectories. FIG. 13(b) Most descriptors of nuclear FP-RelA dynamics in panel (a) do not change significantly even in the presence of a high concentration of Compound 1. Box (first and third quartile), whisker (1.5 times interquartile range), and median (red centre line) are shown for cells pre-treated with DMSO (blue) or compound 1 (orange). Red minus and plus symbols respectively indicate the absence or presence of TNF. Double stars indicate statistically significant p-values based on permutation test shown in (c). FIG. 13(c) Histograms measuring the difference between the means for 106 permutations of data from the TNF-only control and 10 uM of Compound 1. Red line indicates the difference between the means of un-permuted data and corresponding p-values (two-tailed) are listed for each permutation test.

FIG. 16(a) Representative live-cell images of cells stained with Calcein AM, a cell-permeable compound that becomes fluorescent only in viable cells, and Ethidium homodimer 1 which accumulates in the nucleus of dead cells only. Cells were exposed to either DMSO (top) or Bay 11-7082 (bottom) for 24 hours before imaging. Bay 11-7082 is a common NF-kB inhibitor with a mode of action that prevents activation of IKK kinases. Cells were also stained with Hoechst 33342 to assist with nuclear segmentation. Scale bar 20 μm. FIG. 16(b) Example scatterplot for distributions of fluorescence measured in the nucleus of single cells exposed to DMSO (left, orange squares) or Bay 11-7082 (right, blue circles). Cells positive for Ethidium homodimer fluorescence and with low Calcein AM fluorescence were gated (red box) to identify dead cells. The remaining cells outside of the gate were considered alive. The fraction of surviving cells is quantified in FIG. 16(c) for the indicated duration of exposure conditions. Data shown for 3 biological replicates, ± SEM. On average, n=1600 single cells were measured per condition for each replicate.

FIG. 19(a) Western blot of IKKγ in lysates from CRISPR-modified U2OS cells in the indicated conditions. Minus and plus symbols respectively indicate the presence or absence for each of TNF (red), compound 2 (tan), and compound 3 (teal). FIG. 19(b) Quantification of Actin-corrected IKK band intensity, normalized to control cells that were not pre-treated with compounds (gray), suggest that the presence of compounds 2 (tan) and 3 (teal) downregulate the expression of IKKγ. Indicated p-values (two-tailed) calculated from t tests of biological triplicates (indicated by dot plots). ± standard deviation.

DETAILED DESCRIPTION

Figures 1A, 1B, 1C:
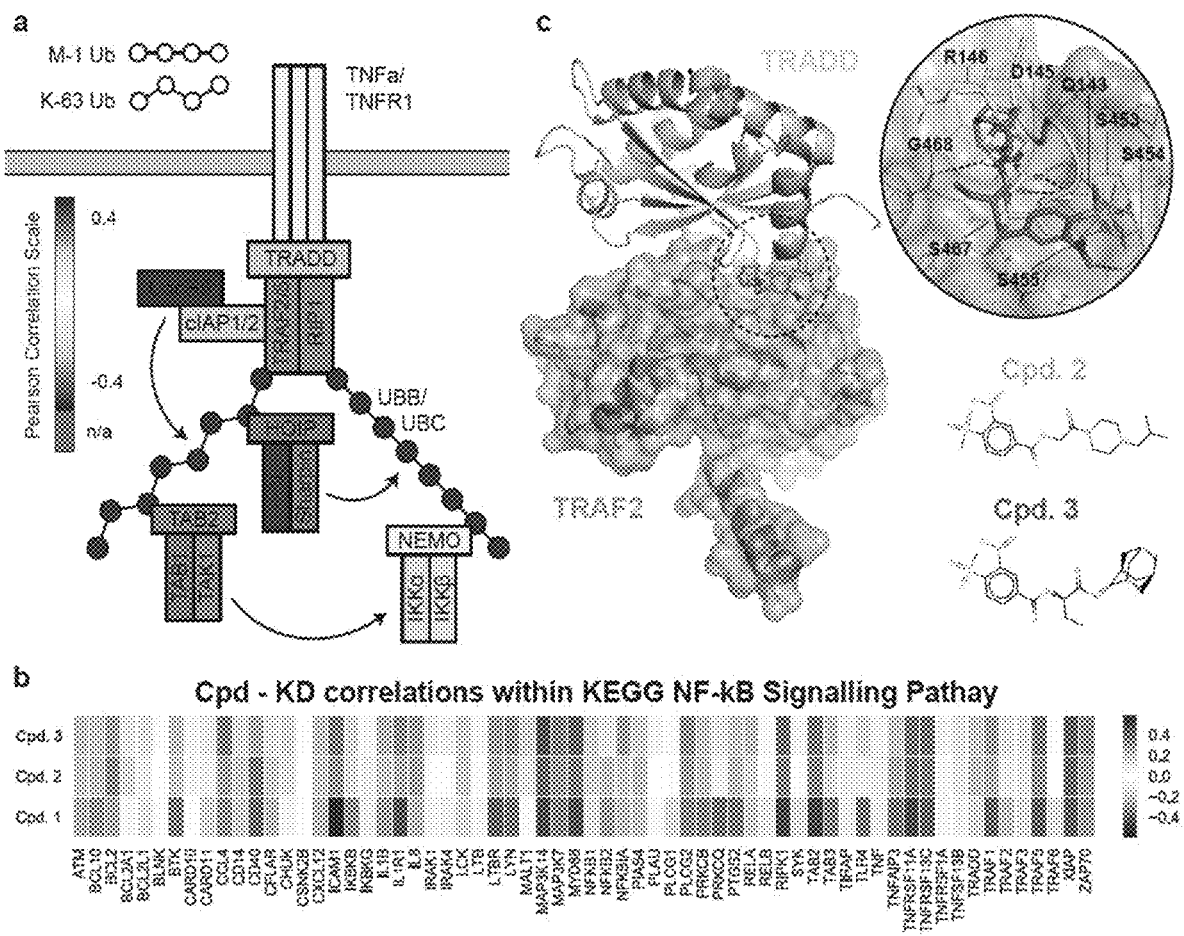
FIGS. 1A-1C shows small molecule treatments produce transcriptional responses in that correlate with genetic knockdowns of proteins involved in NF-kB signaling.

A dynamic and complex network of interacting proteins regulate cellular behavior. Traditional "target-centric" drug development strategies prioritize single-target potency in vitro to modulate key signaling pathway components within the network and produce a desired phenotype. Target-centric strategies use biochemical assays to optimize specificity and affinity of small molecules for a protein class, such as protein kinases, or a specific enzyme. In some cases, an effective inhibitor is comparable with gene knockdown that reduces or completely removes the target protein from the network. However, given that pleiotropy is prevalent among disease-associated proteins, compounds that disrupt specific protein-protein interactions (PPI) while leaving others intact are attractive, especially when complete disruption is detrimental to the cell (Sahni et al., Curr. Opin. Genet. Dev., 23:649-657 (2013); Sahni et al., Cell, 161:647-660 (2015)).

Tumor Necrosis Factor (TNF)-induced NF-kB signaling is an example of a tightly regulated and therapeutically relevant pathway that has resisted target-centric drug discovery. TNF is an inflammatory cytokine that initiates dynamic intracellular signals when bound to its cognate TNF receptor (TNFR1). In response to TNF, the IkB-kinase (IKK) complex is rapidly recruited from the cytoplasm to poly-ubiquitin scaffolds near the ligated receptor where it is activated through induced proximity with its regulatory kinase, TAK1 (Clark et al., Nat. Rev. Mol. Cell Biol., 14: 673-685 (2013); Haas et al., Mol. Cell, 36: 831-844 (2009); Hayden, M. S. & Ghosh, S., Cell, 132:344-362 (2008); Hsu et al., Immunity, 4:387-396 (1996); Kulathu et al., Nat. Struct. Mol. Biol., 16:1328-1330 (2009); Ikeda et al., Nature, 471: 637-641 (2011); Ea et al., Mol. Cell, 22:245-257 (2006)). When fully assembled, the mature TNFR1 complex (FIG. 1a) is a master regulator of inflammation-dependent Nuclear Factor kB (NF-kB) signaling. Nuclear Factor kB inhibitor proteins (IkB) are degraded soon after phosphorylation by activated IKKs, and the NF-kB transcription factor accumulates in the nucleus to regulate TNF-induced transcription. Since changes in the subcellular localization of IKK and NF-kB transmit stimulus-specific information (Lee et al., Mol. Cell, 53:867-879 (2014); Lee et al., Sci. Rep., 6:39519 (2016); Tarantino et al., J. Cell. Biol., 204: 231-245 (2014); Zhang et al., Cell. Syst., 5:638-645 e635 (2017)), these dynamic features can be used to demonstrate pharmacologic alterations to inflammatory signaling (Behar et al., Cell, 155: 448-461 (2013)).

Chemicals that modulate inflammation-dependent IKK and NF-kB signals are of considerable therapeutic interest. Activated NF-kB regulates expression for hundreds of genes that mediate signals for inflammation, proliferation, and survival (Hayden, M. S. & Ghosh, S. Genes Dev 18, 2195-2224 (2004); Kasibhatla et al., Mol. Cell., 1:543-551 (1998); Lawrence, T., Cold Spring Harb Perspect. Biol., 1: a001651 (2009); Pahl, H. L., Oncogene, 18:6853-6866 (1999); Tak, P. P. & Firestein, G. S., J. Clin. Invest., 107:7-11 (2001); Wajant, H. & Scheurich, P., FEBSI J., 278:862-876 (2011)) and its deregulation is linked to chronic inflammation in addition to the development and progression of various cancers (Lewis, C. E. & Pollard, J. W., Cancer Res., 66: 605-612 (2006); Staudt, L. M., Cold Spring Harb. Perspect. Biol., 2: a000109 (2010); Marx, J., Science, 306: 966-968 (2004); Schottenfeld, D. & Beebe-Dimmer, J., CA Cancer J. Clin., 56:69-83 (2006)). As pleiotropic proteins, IKK and NF-kB are poor targets for inhibitors because they provide basal activity as survival factors independent of inflammatory signaling (Dave et al., J. Immunol., 179: 7852-7859 (2007)) and their genetic disruption can be lethal (Li et al., Science, 284: 321-325 (1999); Li, Q. & Verma, I. M., Nat. Rev. Immunol., 2: 725-734 (2002)). The complexity of the pathway and the difficulty of modulating specific protein-protein interactions in vivo exacerbates the challenges of drugging this pathway in the cell (DiDonato et al., *Immunol. Rev.*, 246: 379-400 (2012)). Not surprisingly, there are no clinically approved small-molecule inhibitors of NF-kB pathway components.

The present disclosure is directed to the surprising discovery of new small-molecule inhibitors of NF-kB pathway components and methods of using the same.

I. Compounds

Some embodiments include a compound represented by formula (I):

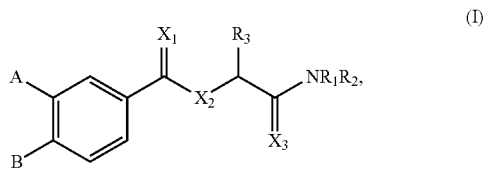

or a salt, solvate, hydrate or prodrug thereof, wherein: A is an azinic acid; B is an alkyl sulfonyl; $X_1$ and $X_3$ are independently selected from O, NOH, NO-alkyl, $CF_3$, and $C(CN)_2$; $X_2$ is selected from O, NH, and NF; $R_1$ is H or alkyl and $R_2$ is an optionally substituted alkyl or cycloalkyl, or $R_1$ and $R_2$ together form an optionally substituted 5- or 6-membered heterocycle; and $R_3$ is selected from H, F, and an optionally substituted alkyl.

In some embodiments, the compound represented by formula (I) does not include:

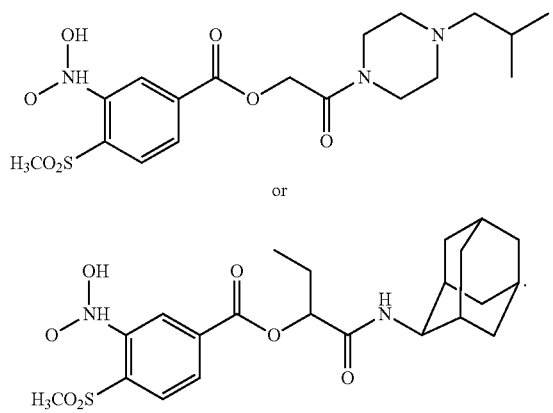

In certain embodiments, B is a methyl sulfonyl or ethyl sulfonyl.

In some embodiments, —$NR_1R_2$ is represented by:

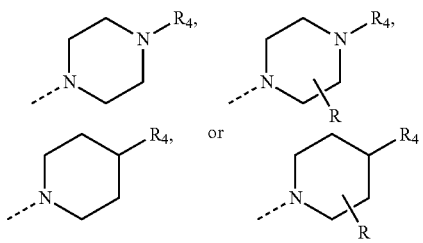

wherein $R_4$ is an optionally substituted alkyl, alkene, alkyne, or —$COOR_5$, where $R_5$ is an optionally substituted alkyl or cycloalkyl. and R is a non-H substituent, for example halo, hydroxyl, O-alkyl, alkyl, alkene, alkyne, or —$COOR_5$. Some embodiments, include more than one R substitution (e.g., 2, 3, or 4).

In some embodiments, $R_2$ is an optionally substituted alkyl or cycloalkyl. For example, certain embodiments include where $R_2$ is an optionally substituted cyclopropyl, cyclobutyl, cyclocyclopentyl or cyclohexyl. The cyclopropyl, cyclobutyl, cyclopentyl or cyclohexyl may be substituted, for example, with one or more halo, hydroxyl, O-alkyl, alkyl, alkene, alkyne, or —$COOR_5$. Other embodiments include where $R_2$ is an optionally substituted alkyl, such as a C1-C10 alkyl or C1-C6 alkyl. The alkyl may be linear or branched, and the alkyl may be substituted, for example, with one or more halo, hydroxyl, O-alkyl, cycloalkyl, alkene, alkyne, or —$COOR_5$.

In some embodiments, $X_1$, $X_2$ and $X_3$ are each O. In other embodiments, one of $X_1$ and $X_3$ is O and the other is selected from O, NOH, NO-alkyl, $CF_3$, and $C(CN)_2$.

In some embodiments, $R_3$ is H. In other embodiments, $R_3$ is an optionally substituted alkyl, such as a C1-C10 alkyl or C1-C6 alkyl. The alkyl may be linear or branched, and the alkyl may be substituted, for example, with one or more halo, hydroxyl, O-alkyl, cycloalkyl, alkene, alkyne, or —$COOR_5$.

Some embodiments include a composition comprising a compound represented by formula (I) and a pharmaceutically acceptable carrier. In some embodiments, the composition is suitable for administration to a mammal, e.g., a human.

Dosage Forms. The formulations may conveniently be presented in unit dosage form and may be prepared by any of the methods well known in the art of pharmacy. Any pharmaceutically acceptable dosage form may be employed in the methods of the invention For example, the composition can be formulated into a dosage form (a) selected from the group consisting of liquid dispersions, gels, aerosols, lyophilized formulations, tablets, capsules; and/or (b) into a dosage form selected from the group consisting of controlled release formulations, fast melt formulations, delayed release formulations, extended release formulations, pulsatile release formulations, and mixed immediate release and controlled release formulations; or (c) any combination of (a) and (b). In addition, the composition can be administered via any pharmaceutically acceptable method, such as oral, pulmonary, rectal, colonic, parenteral, intracisternal, intravaginal, intraperitoneal, intravenous, subcutaneous, intramuscular, nebulization, inhalation, ocular, otic, local, buccal, nasal, or topical administration.

II. Methods

Other embodiments of the present disclosure include a method of preventing formation of mature TNFR1 complex, comprising contacting a cell with an effective compound of formula (I). In some embodiments, the contacting is in vitro. In some embodiments, the contacting is in vivo in a subject suffering from a disease caused by blockade of TNF-induced signaling such as rheumatoid arthritis, ankylosing spondylitis, inflammatory bowel disease (e.g., Crohn's disease or ulcerative colitis), and psoriasis. In some embodiments, the contacting is in vivo in a subject suffering from a disease caused by inflammation-associated cancers that are potentiated by TNF-induces NFkB signaling, such as aggressive diffuse large B-cell lymphoma and metastatic carcinomas including tumors of the colon, lung, pancreas, and brain.

Additional embodiments of the present disclosure include a method of inhibiting a TNF-induced nuclear factor kB (NF-kB) inflammation pathway, comprising contacting a cell with a compound of formula (I). In some embodiments, the contacting is in vivo in a subject suffering from a disease caused by blockade of TNF-induced signaling such as rheumatoid arthritis, ankylosing spondylitis, inflammatory bowel disease (e.g., Crohn's disease or ulcerative colitis), and psoriasis. In some embodiments, the contacting is in vivo in a subject suffering from a disease caused by inflammation-associated cancers that are potentiated by TNF-induced NFkB signaling, such as aggressive diffuse large B-cell lymphoma and metastatic carcinomas including tumors of the colon, lung, pancreas, and brain.

Some embodiments include methods of treating a subject (e.g., a human) suffering from a disease caused by blockade of TNF-induced signaling, comprising administering to the subject in need thereof a pharmaceutically effective amount a compound of formula (I). In some embodiments, the disease caused by blockade of TNF-induced signaling such as rheumatoid arthritis, ankylosing spondylitis, inflammatory bowel disease (e.g., Crohn's disease or ulcerative colitis), and psoriasis.

Some embodiments include methods of treating a subject (e.g., a human) suffering from a disease caused by inflammation-associated cancers that are potentiated by TNF-induced NFkB signaling, comprising administering to the subject in need thereof a pharmaceutically effective amount a compound of formula (I). In some embodiments, the disease caused by inflammation-associated cancers that are potentiated by TNF-induced NFkB signaling, is selected from aggressive diffuse large B-cell lymphoma and metastatic carcinomas including tumors of the colon, lung, pancreas, and brain.

Other embodiments include methods for identifying molecules that specifically inhibit a TNF-induced NF-kB inflammation pathway, comprising (1) comparing transcriptional profiles between genetic knockdowns of proteins in the NF-kB signaling pathway and responses of the same cell types to the molecule; (2) calculating a binding mode of the compound through molecular docking calculation. In some embodiments, the method further includes testing inhibitory activity of the compound in vitro.

Other embodiments include methods for identifying one or more molecules from a group of molecules that specifically alters a cellular phenotype, comprising (1) comparing transcriptional profiles between genetic knockdowns of proteins in the phenotype and responses of the same cell types to the group of molecules; (2) selecting the one or more molecule from the group of molecules that alters the cellular phenotype. In some embodiments, the method further includes calculating a binding mode of the one or more molecules selected in step (2) through molecular docking calculation with a biding site in a protein of the cellular phenotype. In some embodiments, the method further includes testing inhibitory activity of the one or more molecules selected in step (2) in vitro. In some embodiments, the method further includes testing for the desired cellular phenotype based on the activity of the one or more molecules selected in step (2) in vitro. In some embodiments, the cellular phenotype includes inhibition of a signaling pathway.

Thus, embodiments herein include a network-centric strategy is to predict small-molecules that act on rate-limiting PPIs in the signaling pathway in silico, and screen them for phenotypes associated with pathway disruption in vivo. Although complete disruption of IKK and NF-kB can have damaging effects on the cell, their dynamics in response to disease-associated inflammatory signals are influenced by over 50 other proteins. Thus, the broader NF-kB network contains numerous entry points for chemicals to impinge on the pathway. Machine learning may be used with gene expression data to provide a synoptic list of likely small-molecule inhibitors of the NF-kB pathway. For a well-defined molecular network, it is shown that pathway-specific inhibitors can be predicted from transcriptomic alterations that are shared between i) exposure to small molecules and ii) genetic knockdowns of the pathway components. Through molecular docking a reduced list of predicted compounds and a mechanism of action may be provided, and evaluation of bioactivity using live-cell experiments that monitor signaling dynamics in single cells may be used.

III. Definitions

The terms "pharmacologically effective amount" or "therapeutically effective amount" of a composition or agent, as provided herein, refer to a nontoxic but sufficient amount of the composition or agent to provide the desired response, such as a reduction or reversal of cancer. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compounds, compositions and methods include the recited elements, but not exclude others. "Consisting essentially of" when used to define compounds, compositions and methods, shall mean excluding other elements of any essential significance to the combination. Thus, a composition consisting essentially of the elements as defined herein would not exclude trace contaminants, e.g., from the isolation and purification method and pharmaceutically acceptable carriers, preservatives, and the like. "Consisting of" shall mean excluding more than trace elements of other ingredients. Embodiments defined by each of these transition terms are within the scope of this technology.

All numerical designations, e.g., pH, temperature, time, concentration, and molecular weight, including ranges, are approximations which are varied (+) or (−) by increments of 1, 5, or 10%. It is to be understood, although not always explicitly stated that all numerical designations are preceded by the term "about." It also is to be understood, although not always explicitly stated, that the reagents described herein are merely exemplary and that equivalents of such are known in the art.

The term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. For example, in some embodiments, it will mean plus or minus 5% of the particular term. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

"Optional" or "optionally" means that the subsequently described circumstance may or may not occur, so that the description includes instances where the circumstance occurs and instances where it does not.

"Pharmaceutically acceptable excipient or carrier" refers to an excipient that may optionally be included in the compositions of the disclosure and that causes no significant adverse toxicological effects to the patient.

"Substantially" or "essentially" means nearly totally or completely, for instance, 95% or greater of some given quantity. In some embodiments, "substantially" or "essentially" means 95%, 96%, 97%, 98%, 99%, 99.5%, or 99.9%.

"Optionally substituted" refers to a group selected from that group and a substituted form of that group. A "substituted" group, refers to that group substituted with any substituent described or defined below. Substituted groups are defined herein. In one embodiment, substituents are selected from, deuterium, $SF_5$, $CF_3$, $OCF_3$, halo, haloaryl, alkoxy, aryloxy, haloalkoxy, haloaryloxy, aryl, benzyl, benzyloxy, heteroaryl, nitrile, $C_1$-$C_6$ alkyl, $C_1$-$C_6$ alkenyl, $C_1$-$C_6$ alkynyl, $C_3$-$C_6$ cycloalkyl, $C_1$-$C_6$ haloalkyl, $C_1$-$C_6$ haloalkenyl, $C_1$-$C_6$ haloalkynyl, $C_3$-$C_6$ halocycloalkyl $C_1$-$C_{10}$ or $C_1$-$C_6$ alkyl, $C_2$-$C_6$ alkenyl, $C_2$-$C_6$ alkynyl, $C_6$-$C_{10}$ aryl, $C_3$-$C_8$ cycloalkyl, $C_2$-$C_{10}$ heterocyclyl, $C_1$-$C_{10}$ heteroaryl, —$N_3$, nitro, —$CO_2H$ or a $C_1$-$C_6$ alkyl ester thereof, haloaryl, alkoxy, aryloxy, haloalkoxy, haloaryloxy, aryl, benzyl, benzyloxy, $C_1$-$C_6$ haloalkyl, $C_2$-$C_6$ haloalkenyl, $C_2$-$C_6$ haloalkynyl, or any of the functional groups described or defined below.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—). A Cx-Cy alkyl will be understood to have from x to y carbons.

"Alkenyl" refers to monovalent straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic unsaturation. Examples of such alkynyl groups include acetylenyl (—C≡CH), and propargyl (—CH$_2$≡CH).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Substituted alkenyl" refers to alkenyl groups having from 1 to 3 substituents, and preferably 1 to 2 sub stituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxyl, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxyl or thiol substitution is not attached to a vinyl (unsaturated) carbon atom.

"Substituted alkynyl" refers to alkynyl groups having from 1 to 3 substituents, and preferably 1 to 2 sub stituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxyl or thiol substitution is not attached to an acetylenic carbon atom.

"Prodrug," of a compound, as used herein, refers to a chemical that when metabolized, turns into the compound.

An animal, subject or patient for diagnosis, treatment, or administration of the compounds if the disclosure thereto, refers to an animal such as a mammal, or a human, ovine, bovine, feline, canine, equine, simian, etc. Non-human animals subject to diagnosis, treatment, or administration thereto of compounds of the disclosure include, for example, simians, murine, such as, rat, mice, canine, leporid, livestock, sport animals, and pets.

A "composition" "pharmaceutical composition" as used herein, intends an active agent, such as a compound as disclosed herein and a carrier, inert or active. The carrier can be, without limitation, solid such as a bead or resin, or liquid, such as phosphate buffered saline.

"Cycloalkyl" refers to cyclic alkyl groups of from 3 to 10 carbon atoms having single or multiple cyclic rings including fused, bridged, and spiro ring systems. The fused ring can be an aryl ring provided that the non-aryl part is joined to the rest of the molecule. Examples of suitable cycloalkyl groups include, for instance, adamantyl, cyclopropyl, cyclobutyl, cyclopentyl, and cyclooctyl.

"Substituted cycloalkyl" and "substituted cycloalkenyl" refers to a cycloalkyl or cycloalkenyl group having from 1 to 5 or preferably 1 to 3 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio.

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through a non-aromatic ring. In one embodiment, the nitrogen and/or sulfur atom(s) of the heterocyclic group are optionally oxidized to provide for the N-oxide, sulfinyl, or sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Pharmaceutically acceptable salt" refers to salts of a compound, which salts are suitable for pharmaceutical use and are derived from a variety of organic and inorganic counter ions well known in the art and include, when the compound contains an acidic functionality, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate (see Stahl and Wermuth, eds., "Handbook of Pharmaceutically Acceptable Salts," (2002), Verlag Helvetica Chimica Acta, Zürich, Switzerland), for a discussion of pharmaceutical salts, their selection, preparation, and use.

"Active molecule" or "active agent" as described herein includes any agent, drug, compound, composition of matter or mixture which provides some pharmacologic, often beneficial, effect that can be demonstrated in vivo or in vitro. This includes foods, food supplements, nutrients, nutraceuticals, drugs, vaccines, antibodies, vitamins, and other beneficial agents. As used herein, the terms further include any physiologically or pharmacologically active substance that produces a localized or systemic effect in a patient. In specific embodiments, the active molecule or active agent includes the compound of formula I, or a pharmaceutically acceptable salt or solvate thereof.

"Substantially" or "essentially" means nearly totally or completely, for instance, 95% or greater of some given quantity. In some embodiments, "substantially" or "essentially" means 95%, 96%, 97%, 98%, 99%, 99.5%, or 99.9%.

Generally, pharmaceutically acceptable salts are those salts that retain substantially one or more of the desired pharmacological activities of the parent compound and which are suitable for in vivo administration. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydroiodic acid, etc.), sulfuric acid, nitric acid, phosphoric acid, and the like.

Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion, or an aluminum ion) or by an ammonium ion (e.g., an ammonium ion derived from an organic base, such as, ethanolamine, diethanolamine, triethanolamine, morpholine, piperidine, dimethylamine, diethylamine, triethylamine, and ammonia).

A solvate of a compound is a solid-form of a compound that crystallizes with less than one, one or more than one molecules of a solvent inside in the crystal lattice. A few examples of solvents that can be used to create solvates, such as pharmaceutically acceptable solvates, include, but are not limited to, water, C1-C6 alcohols (such as methanol, ethanol, isopropanol, butanol, and can be optionally substituted) in general, tetrahydrofuran, acetone, ethylene glycol, propylene glycol, acetic acid, formic acid, and solvent mixtures thereof. Other such biocompatible solvents which may aid in making a pharmaceutically acceptable solvate are well known in the art. Additionally, various organic and inorganic acids and bases can be added to create a desired solvate. Such acids and bases are known in the art. When the solvent is water, the solvate can be referred to as a hydrate. In some embodiments, one molecule of a compound can form a solvate with from 0.1 to 5 molecules of a solvent, such as 0.5 molecules of a solvent (hemisolvate, such as hemihydrate), one molecule of a solvent (monosolvate, such as monohydrate) and 2 molecules of a solvent (disolvate, such as dihydrate).

An "effective amount" or a "pharmaceutically acceptable amount" is an amount sufficient to effect beneficial or desired results. An effective amount can be administered in one or more administrations, applications or dosages and is determined by the system in which the drug or compound is delivered, e.g., an effective amount for in vitro purposes is not the same as an effective amount for in vivo purposes. For in vivo purposes, the delivery and "effective amount" is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. In general, one will desire to administer an amount of the compound that is effective to achieve a serum level commensurate with the concentrations found to be effective in vivo. These considerations, as well as effective formulations and administration procedures are well known in the art and are described in standard textbooks.

As used herein, "treating" or "treatment" of a disease in a patient refers to (1) preventing the symptoms or disease from occurring in an animal that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of this technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

As used herein, the term "contacting" intends bringing the reagents into close proximity with each other so that a chemical or biochemical reaction can occur among the reagents. In one aspect, the term intends admixing the components, either in a reaction vessel or on a plate or dish. In another aspect, it intends in vivo administration to a subject.

The term "binding" or "binds" as used herein are meant to include interactions between molecules that may be covalent or non-covalent which, in one embodiment, can be detected using, for example, a hybridization assay. The terms are also meant to include "binding" interactions between molecules. Interactions may be, for example, protein-protein, antibody-protein, protein-nucleic acid, protein-small molecule or small molecule-nucleic acid in nature. This binding can result in the formation of a "complex" comprising the interacting molecules. A "complex" refers to the binding of two or more molecules held together by covalent or non-covalent bonds, interactions or forces.

Throughout this disclosure, various publications, patents and published patent specifications are referenced by an identifying citation. The disclosures of these publications, patents and published patent specifications are hereby incorporated by reference into the present disclosure in their entirety to more fully describe the state of the art to which this invention pertains.

The practice of the present technology will employ, unless otherwise indicated, conventional techniques of organic chemistry, pharmacology, immunology, molecular biology, microbiology, cell biology and recombinant DNA, which are within the skill of the art. See, e.g., Sambrook, Fritsch and Maniatis, *Molecular Cloning: A Laboratory Manual*, $2^{nd}$ edition (1989); *Current Protocols in Molecular Biology* (F. M. Ausubel et al., eds., (1987)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, a Laboratory Manual*, and *Animal Cell Culture* (R. I. Freshney, ed. (1987)).

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. The present examples, along with the methods described herein are presently representative of embodiments and are exemplary, and are not intended as limitations on the scope of the disclosure. Changes therein and other uses which are encompassed within the spirit of the disclosure as defined by the scope of the claims will occur to those skilled in the art.

EXAMPLES

Example 1

Figure 6:
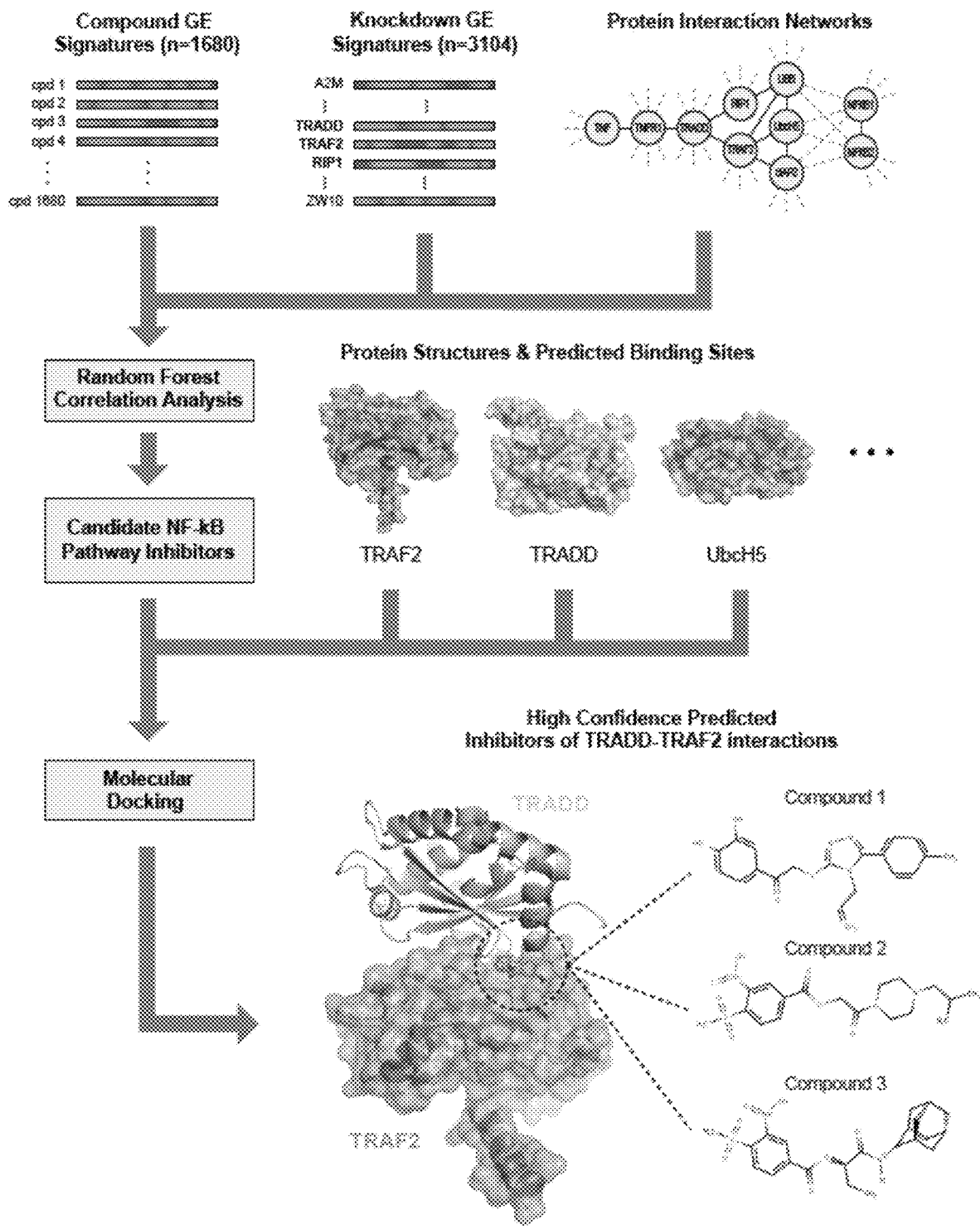
FIG. 6 shows a prediction pipeline used to identify small molecule inhibitors of TNF-inducible NF-kB signaling. Pipeline input includes cell-specific gene expression (GE) signatures from 1680 bioactive small molecules and 3104 gene knockdown, taken from the LINCS L1000 dataset (Keenan et al., *Cell Syst.*, 6:13-24 (2018)), and the protein interaction networks of these genes, inferred from their BioGrid (Chatr-Aryamontri et al., *Nucleic Acids Res.*, 43:D470-478 (2015)). Correlations between compound and knockdown GE signatures and their distribution on the TNF-inducible NF-kB pathway are evaluated by a random forest classifier to predict candidate inhibitors. Structural models of pathway proteins are mined from the PDB (Berman et al., *Nucleic Acids Res.*, 28:235-242 (2000)) and used as molecular docking targets for candidates. Docking results are assessed to identify high-confidence predicted inhibitors. Results are shown for TRADD-TRAF2 interactions in this study.

Differential Gene Expression Signatures Identify Small Molecules that Correlate with NF-kB Signaling To demonstrate a network-centric strategy for targeting TNF-induced NF-kB signaling, differential gene expression signatures from the NIH Library of Integrated Network-Based Cellular Signatures (LINCS) L1000 dataset (Keenan et al., *Cell Syst.*, 6:13-24 (2018)) was reviewed. Transcriptional profiles between genetic knockdowns of proteins in the NF-kB signaling pathway and responses of the same cell types to thousands of distinct bioactive compounds were compared. Using a random forest classification model trained using FDA-approved drugs, compounds whose transcriptomic perturbations resembled genetic disruption were identified. For each compound, the probability of a compound-protein interaction was evaluated in terms of 'direct' correlation with the knockdown signatures, and 'indirect' correlations with knockdown signatures of other proteins in the network for 4 or more cell lines (see Pabon et al., *PLoS Comput. Biol.*, 14 (2018) for detailed explanation of the approach). Note that disruption of a physical target is expected to cause similar gene expression profiles as downstream or upstream perturbations in the same subnetwork. Hence, a compound that disrupts TRADD or TRAF2 in FIG. 1a might have similar signatures to the knockdown of genes in the pathway such as TNFR1, UBC, or NEMO. Here, compounds that suggest chemical inhibition acts broadly within a subnetwork (FIG. 6) to drug the NF-kB signaling pathway.

Figure 7:
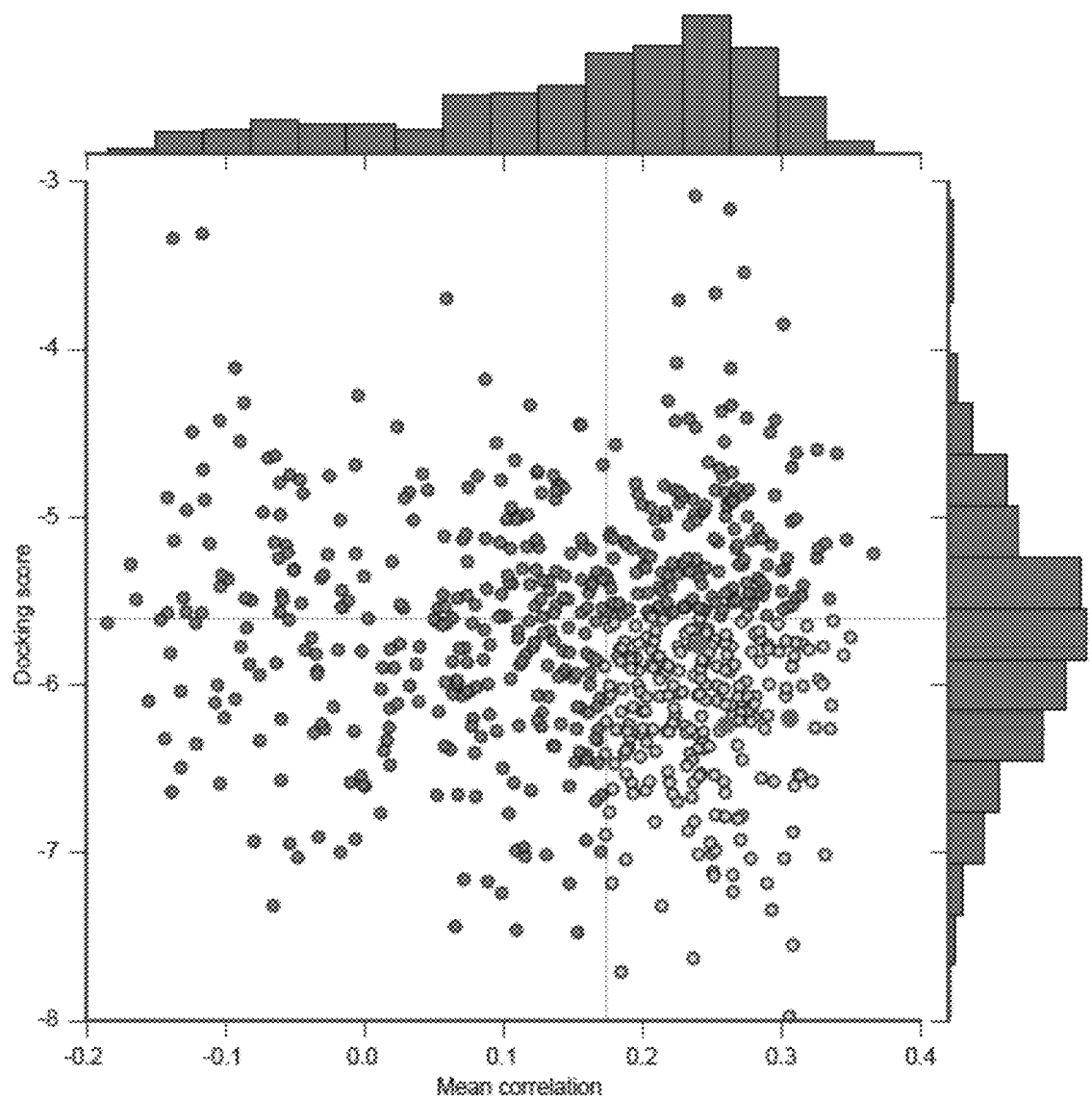
FIG. 7 shows enrichment of NF-kB pathway disruptors. Horizontal axis shows the average Pearson correlation between the gene expression profile of the 717 compounds predicted to target TRAF2, TRADD or RIPK1 (Pabon et al., *PLoS Comput. Biol.*, 14 (2018)) and the genes in the TNFR1 complex (FIG. 1(a)) present in the L1000 LINCS dataset (TRADD, TRAF2, TRAF5, UBB, UBC, RIPK1, TAB2, TAB3, UBE2D1, BIRC2, BIRC3, RBCK1, MAP3K7, IKBKB, CHUK, IKBKG). Vertical axis shows the Vina score (negative is better) of the docked poses(Ye et al., *J. Comput. Aided Mol. Des.*, 30: 695-706 (2016)) on the TRAF2-TRADD binding interface. Highlighted in red are the three compounds selected for testing that lie among 180 compounds in the top 50% of both axes. Many of the best Vina scores correspond to unusually large compounds with poor ligand efficiency (Kuntz et al., *Proc Natl Acad Sci USA*, 96: 9997-10002 (1999)).

A PPI inhibitory peptide that competes with recruitment of catalytic IKK subunits at ubiquitin scaffolds was previously shown to inhibit inflammatory NF-kB activation and disease progression in a murine model for inflammatory-bowel disease (Dave et al., *J. Immunol.*, 179: 7852-7859 (2007); Shibata et al., *J. Immunol.*, 179: 2681-2685 (2007)). It was reasoned that any compounds that disrupt the mature TNFR1 complex, particularly at the level of TRADD, TRAF2, and RIP1, will prevent TNF-mediated IKK recruitment and nuclear translocation of NF-kB. Transcriptional signatures for 717 unique compounds showed strong correlations with genetic knockdowns of TRADD, TRAF2, and RIP1. From this initial set, potential pathway inhibitors were identified as compounds that also correlated with genes in the mature TNFR1 complex (FIG. 1*a*). Specifically, candidate inhibitors were ranked by their mean Pearson correlation with NF-kB knockdowns to assist selection of compounds for additional screening (FIG. 7).

Example 2

Small Molecules are Predicted to Target Core PPIs in the Mature TNFR1 Complex

Molecular docking was used to further refine the list of candidate compounds and predict mechanism of action against proteins in the TNFR1 signaling complex. The 717 candidate molecules described above were docked with domain structures available in the PDB for TRAF2, TRADD, and RIPK1. TRAF2 emerged as a promising target because, contrary to the other proteins, co-crystal structures of TRAF2 are available. Namely, the protein-protein interaction between TRAF2 and both TRADD (PDB code 1F3V (Park et al., *Cell*, 101:777-787 (2000))) and a TNFR2 peptide (PDB code 1CA9 (Park et al., *Nature*, 398: 533-538 (1999))) have been characterized. Both co-crystals indicate a well-defined binding site, which was used to visually screen the top scoring compounds based on both Pearson correlation and binding scores (n=180 compounds; see FIG. 7). Three compounds whose binding modes replicate native contacts in the TRADD-TRAF2 protein complex were selected for testing: (1) BRD-K43131268, (2) BRD-K95352812, and (3) BRD-A09719808. For compounds 1, 2, and 3 respectively, predicted targets from a genetic knockdown gene expression dataset (Pabon et al., *PLoS Comput. Biol.*, 14 (2018)) included: TRAF2, UBC, NFKB1, and RIP1; TRAF6, NEMO, TRAF2, NFKB1, UBC, TAB2, and IKKβ; and, NFKB1, TRAF2, UBC, UBB and NEMO. Furthermore, compounds 2 and 3 showed significant correlations with both HOIL, TAK1, cIAP1/2 and UbcH5 knockdowns (FIG. 1*a*) and their corresponding transcriptional profiles of genes in the Nf-Kb pathway (FIG. 1*b*). Compounds 2 and 3 also had similar chemical structures (FIG. 1*c*), strongly suggesting a similar mechanism of action.

Figure 8:
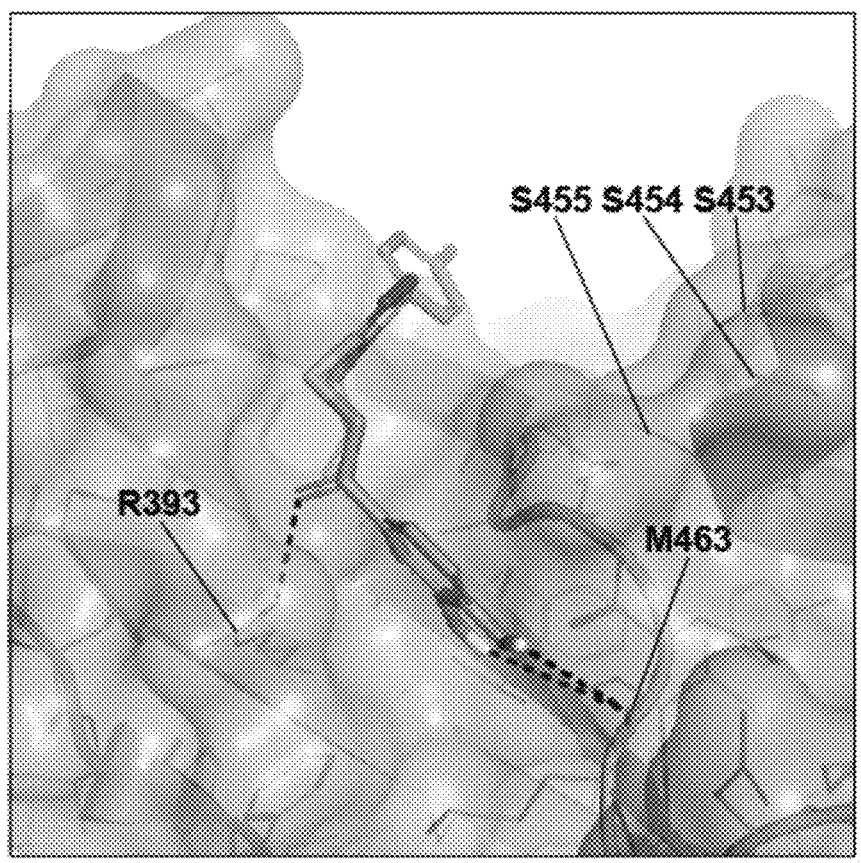
FIG. 8 shows docking of compounds. Predicted binding mode of Compound 1 (orange) to TRADD-binding interface of TRAF2 (green). Hydrogen bonds are indicated with dotted lines.

Compounds 2 and 3 formed hydrogen bond contacts with TRAF2 residues S453, S454, S455, and S467, which are predicted to compete with TRADD interface residues Q143, D145, and R146 based on the co-crystal (FIG. 1*c*). Compound 3 is predicted to bind stronger due to the extra hydrogen bond formed by its amide group with TRAF2 residue G468. Of note, all these TRAF2 residues are conserved in TRAF5. Competitive binding should disrupt the native TRADD-TRAF2/5 PPI interface and could prevent maturation of the full TNFR1 signaling complex by promoting dissociation or allosteric stabilization of a non-native conformation. The predicted binding mode of compound 1 is less specific and did not form any of the contacts described above (FIG. 8).

Figures 2A, 2B:
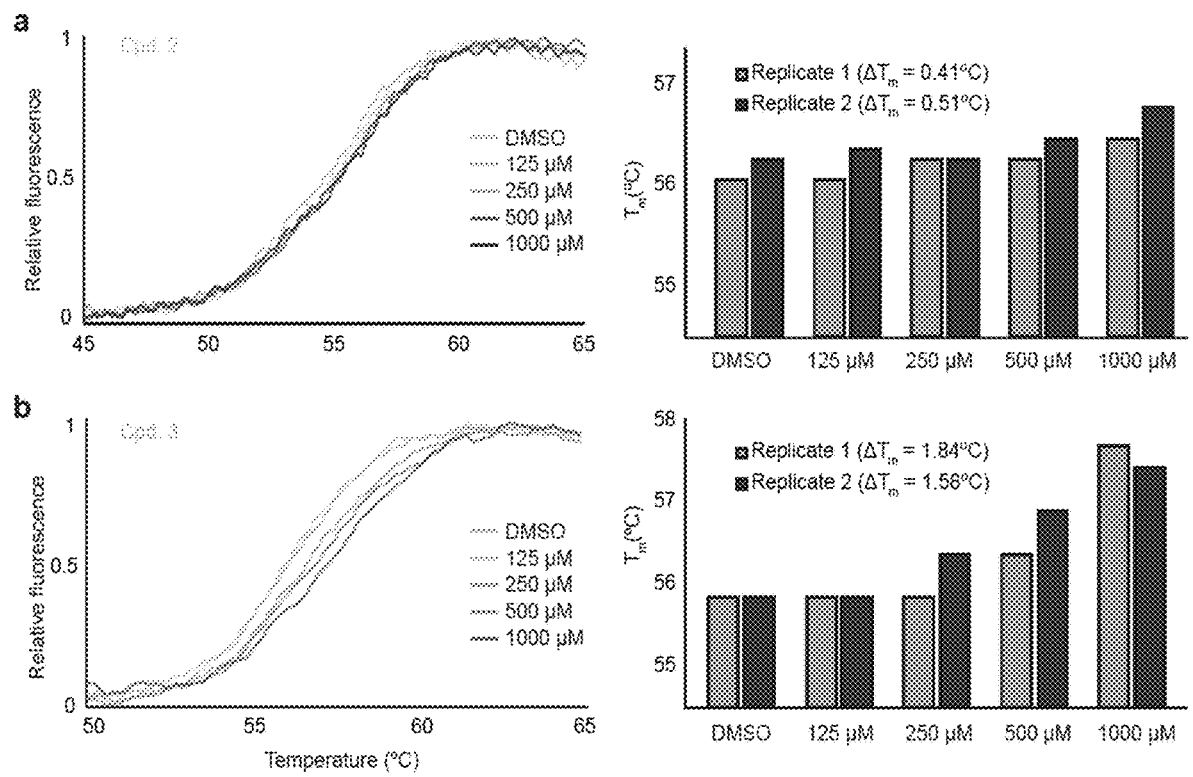
FIGS. 2A-2B shows thermal shift assays indicating moderate dose-dependent stabilization of TRAF2 by compounds 2 and 3. Normalized melt curves (left) and melting temperature ($\Delta t_m$; right) of full length TRAF2 were recorded in the presence of DMSO or indicated concentrations of FIG. 2(a) compound 2 and FIG. 2(b) compound 3. The rightward shift of the melt curve in the presence of compounds, quantified by the $\Delta t_m$ in replicate experiments, suggest increased thermal stability of the protein-compound complex.
Figures 9A, 9B:
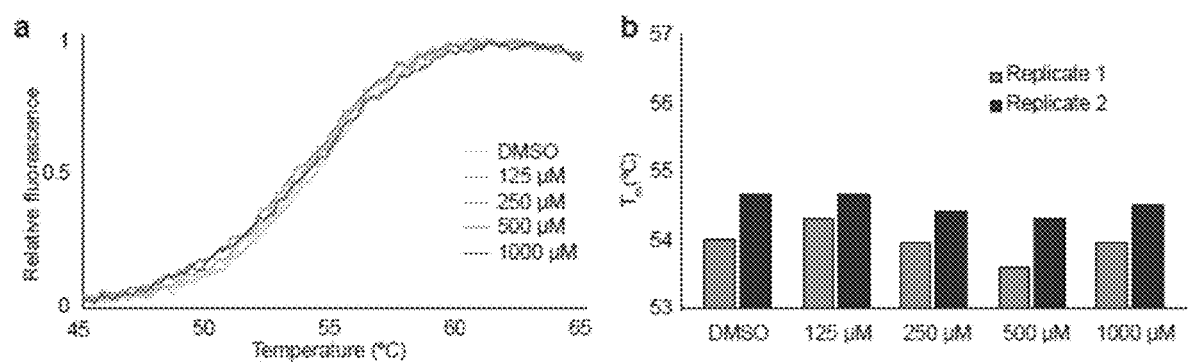
FIGS. 9A-9B shows thermal shift assays indicating no clear effect of Compound 1 on TRAF2 stability.

To test whether the compounds interact with TRAF2 in vitro, the thermal stability of purified TRAF2 in the presence of each compound was measured. Thermal shift assays showed that compounds 2 and 3 respectively exert a subtle to moderate dose-dependent stabilizing effect on full length TRAF2 (FIG. 2*a, b*), suggesting direct compound-protein binding. In contrast, compound 1 did not show a clear trend (FIG. 9). The observed thermal shifts are consistent with the relatively small stabilizing effect that the compounds are expected to exert on the stable trimer formed by the soluble full length TRAF2 protein (Park et al., *Nature*, 398:533-538 (1999)). Together, these data suggest that Compounds 2 and 3 may impinge on TNF-induced signaling.

Example 3

Figures 3A, 3B, 3C, 3D:
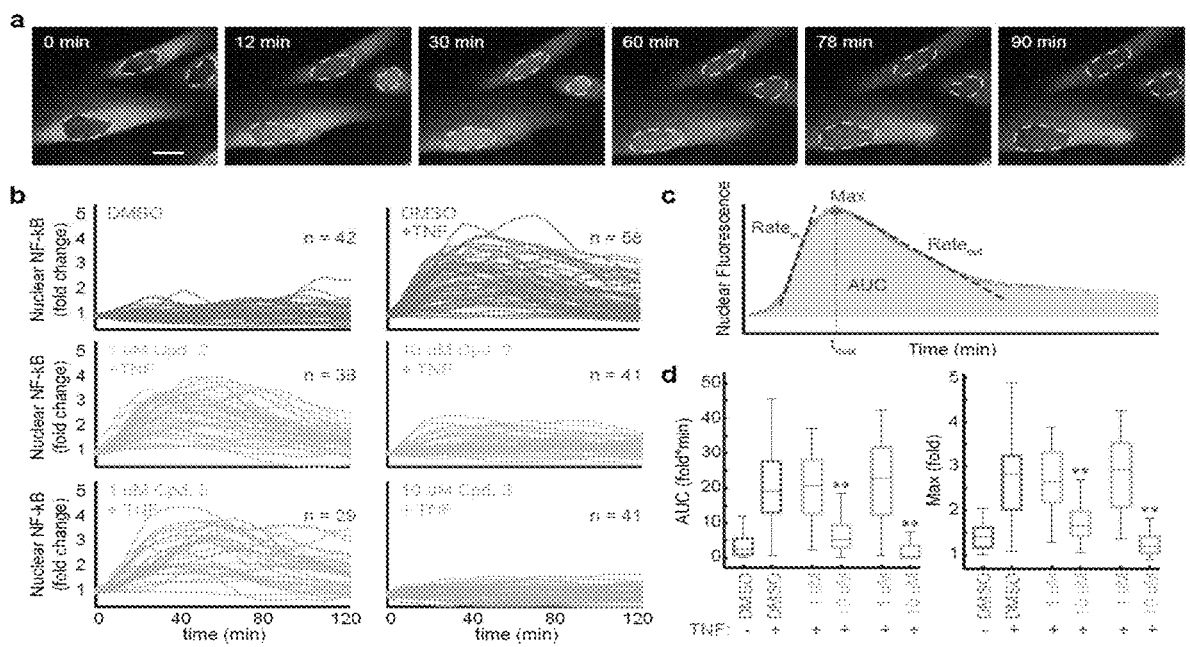
FIGS. 3A-3D shows small molecule disruptors of NF-kB signaling reduce TNF-induced nuclear translocation of NF-kB.
Figures 10A, 10B:
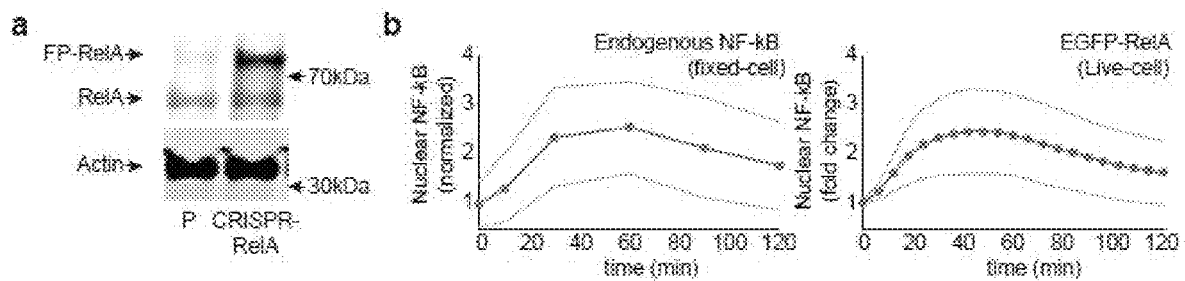
FIGS. 10A-10B shows quantification of FP-RelA expression in U2OS cells.

Small Molecules Disrupt the TNF-Induced Dynamics of Nuclear NF-kB Localization in Single Cells A determination whether the compounds are effective inhibitors of NF-kB signaling in living cells was pursued. For this example, the endogenous gene locus for the transcriptionally active RelA subunit of NF-kB was modified using CRISPR/Cas9 to encode a fluorescent protein (FP) fusion in U2OS cells (FIG. 10), a cell line that forms IKK-recruiting polyubiquitin scaffolds in response to TNF (Tarantino et al., *J. Cell. Biol.*, 204:231-245 (2014)). Responses of single cells exposed to TNF showed transient and variable translocation of NF-kB into the nucleus when measured from time-lapse images (FIG. 3*a*), comparable with other human cancer cell lines that express FP-RelA fusions (Lee et al., *Mol. Cell.*, 53:867-879 (2014); Zhang et al., *Cell. Syst.*, 5:638-645 e6352017); Wong et al., *Cell. Rep.*, 22:585-599 (2018)). When cells were pre-treated with compounds 2 and 3 before exposure to TNF, nuclear mobilization of NF-kB was reduced with increasing concentration of the inhibitory compound (FIG. 3*b*).

Figures 11A, 11B, 11C:
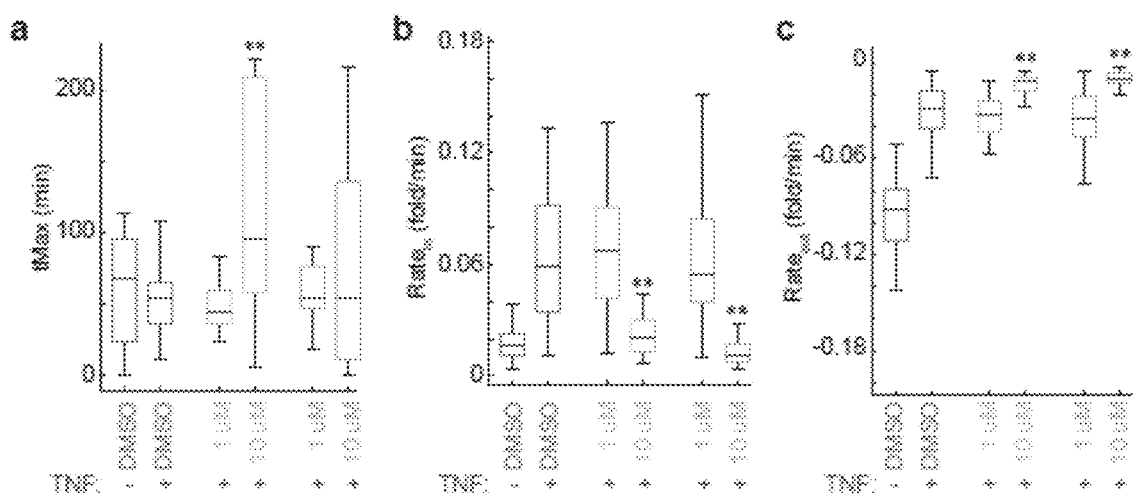
FIGS. 11A-11C shows other descriptors of nuclear FP-RelA. Box (first and third quartile) and whisker (1.5 times interquartile range) plots for descriptors FIG. 11(a) $t_{max}$, FIG. 11(b) $Rate_{in}$, and FIG. 11(c) $Rate_{out}$ exposed to indicated conditions of TNF (10 ng/mL) with either DMSO (blue), compound 2 (tan), or compound 3 (teal). Red center line indicate the median. Double stars indicate statistically significant p-values (two-tailed) based on permutation test (see FIG. 12). Red minus and plus symbols respectively indicate the absence or presence of TNF.
Figures 12A, 12B:
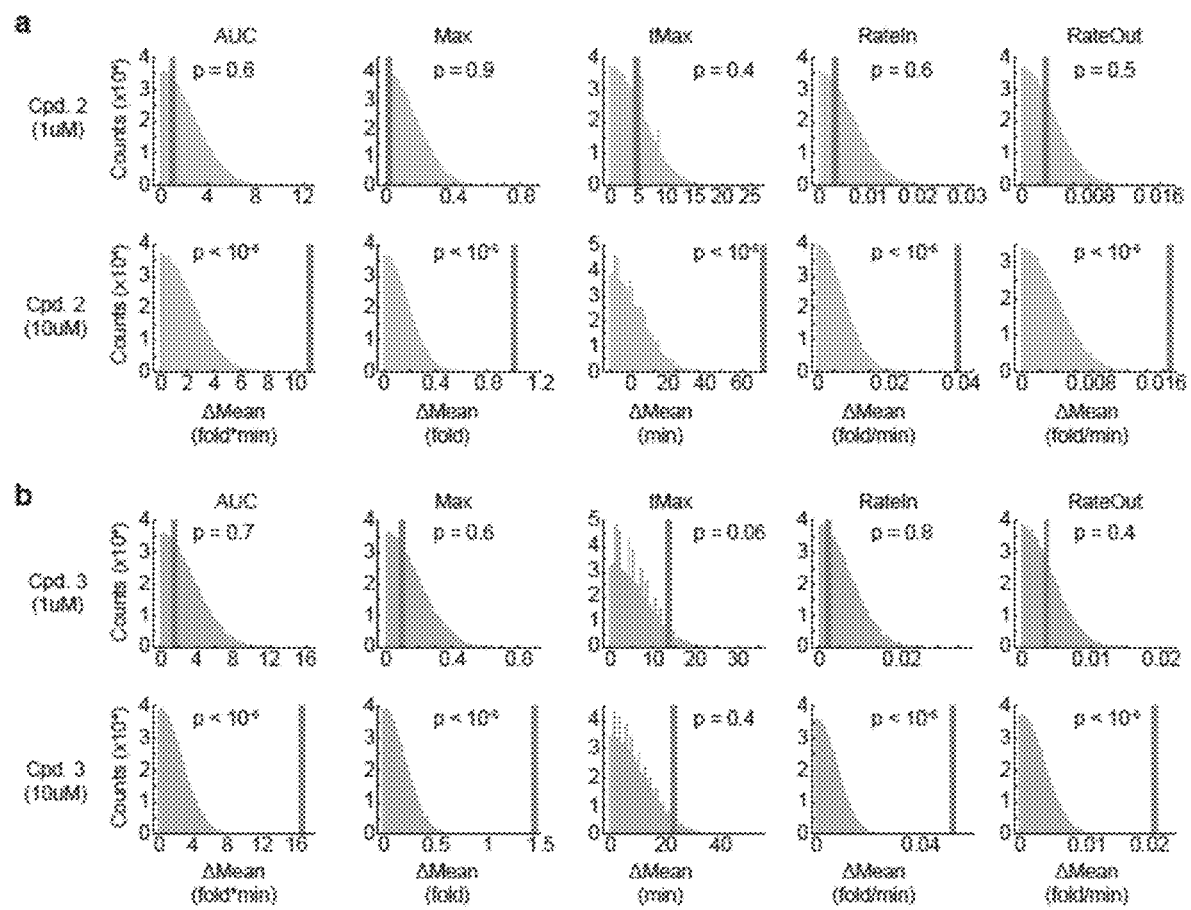
FIGS. 12A-12B shows permutation tests for significance of nuclear FP-RelA descriptors. Histograms measuring the difference between the means for $10^6$ permutations of data from the TNF-only control and TNF with indicated concentrations of FIG. 12(a) Compound 2 (tan distributions) and FIG. 12(b) Compound 3 (teal distributions). Red line indicates the difference between the means of un-permuted data and corresponding p-values (two-tailed) are listed for each permutation test.
Figures 13A, 13B, 13C:
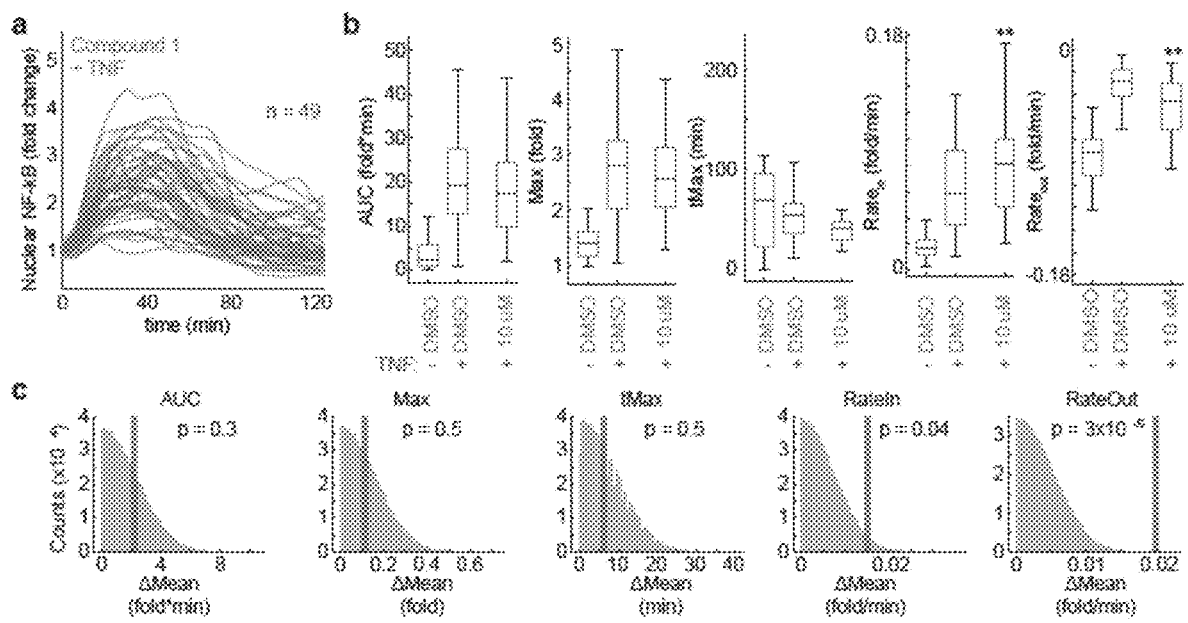
FIGS. 13A-13C shows that Compound 1 does not have a significant effect on most descriptors of FP-RelA translocation.
Figures 14A, 14B:
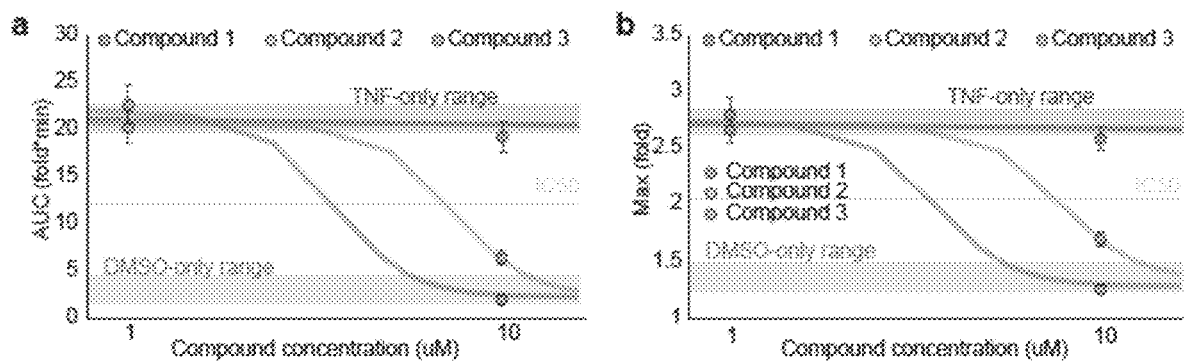
FIGS. 14A-14B shows dose-dependent inhibition of nuclear NF-kB dynamics. Plots from single cell descriptors data in FIG. 3 for the FIG. 14(a) 'Area Under the fold change Curve' and FIG. 14(b) the 'Maximum Fold change'. For each descriptor, the response to TNF-only defines the upper limit of the average cellular response (top red band) and the response to DMSO only defines the lower limit (lower blue band). Plots of the mean and SEM of cellular responses in the presence of Compounds 1, 2, and 3 at the indicated concentration show that the IC50 for Compounds 1 and 2 is between 1 and 10 uM. Adjoining lines guide the eye across a hypothetical dose-response curve.

To quantify the compounds' effect on NF-kB dynamics, each single-cell trajectory was decomposed into a series of descriptors (FIG. 3*c*) that transmit information within the cell about extracellular cytokine concentrations (Zhang et al., *Cell. Syst.*, 5:638-645 e635 (2017)). Descriptors of NF-kB dynamics that transmit the most information about TNF, including the 'area under the fold change curve' ('AUC') and the 'Maximum fold change' ('Max'), were significantly less when cells were pretreated with 10 μM of compound 2 or 3 before the addition of TNF (FIG. 3*d*). Other descriptors showed a similar pattern of inhibition when exposed to 10 μM of either compound prior to TNF stimulation (FIGS. 11 and 12). By contrast, aside from subtle alterations to the rates of nuclear NF-kB mobilization, compound 1 did not significantly alter the overall TNF-induced dynamics of nuclear NF-kB (FIG. 13). These data suggest that compounds 2 and 3 restrict the signaling network upstream of NF-kB activation with low micromolar potency (FIG. 14).

Figures 4A, 4B:
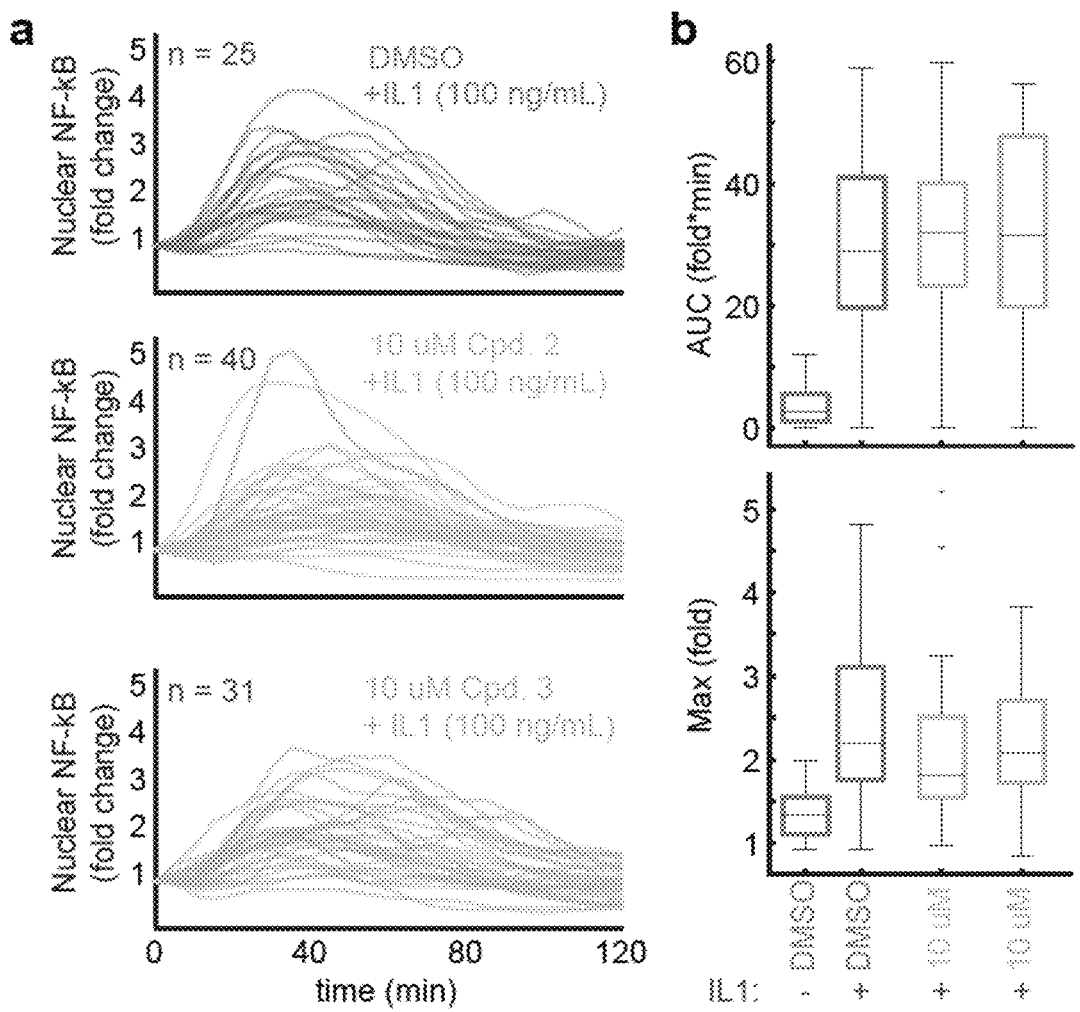
FIGS. 4A-4B shows that compounds do not alter dynamics of nuclear NF-kB in response to IL1.
Figures 15A, 15B:
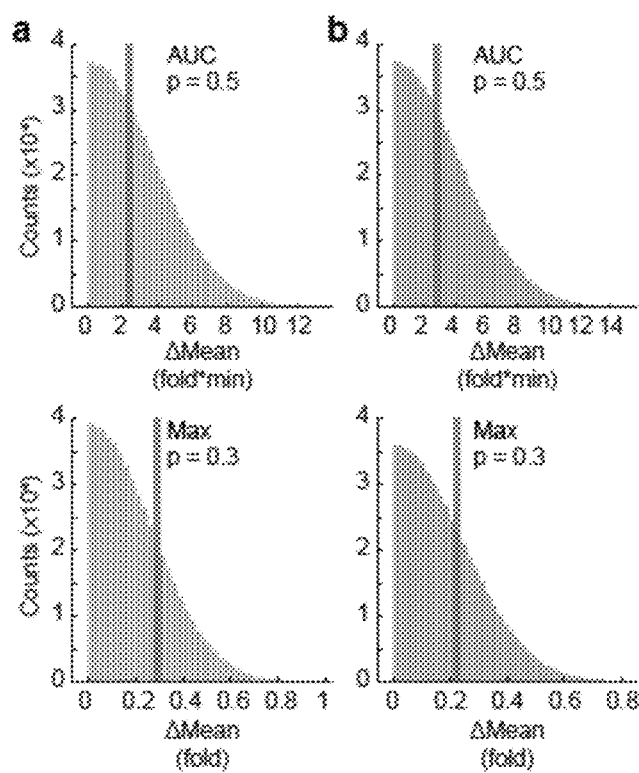
FIGS. 15A-15B shows permutation tests for descriptors for dynamics of nuclear NF-kB in response to IL1. Histograms measuring the difference between the means of indicated descriptors for $10^6$ permutations of data from the IL1-only control and IL1 in the presence of 10 uM of FIG. 15(a) Compound 2 (tan) and FIG. 15(b) Compound 3 (teal). Red line indicates the difference between the means of un-permuted data and corresponding p-values (two-tailed) for the permutation test demonstrate that the descriptors are not significantly altered.
Figures 16A, 16B, 16C:
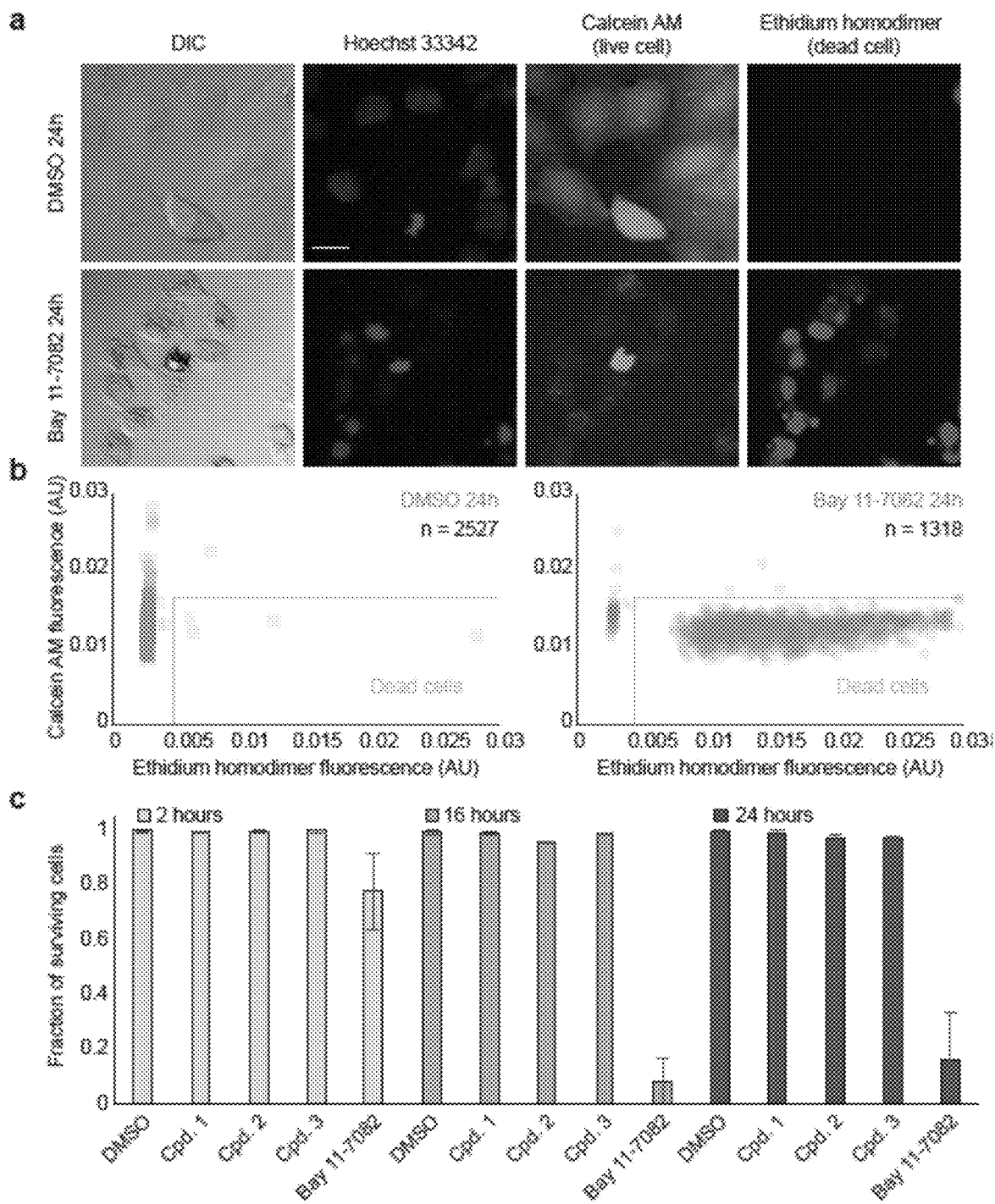
FIGS. 16A-16C shows that compounds have low cytotoxicity.
Figure 17:
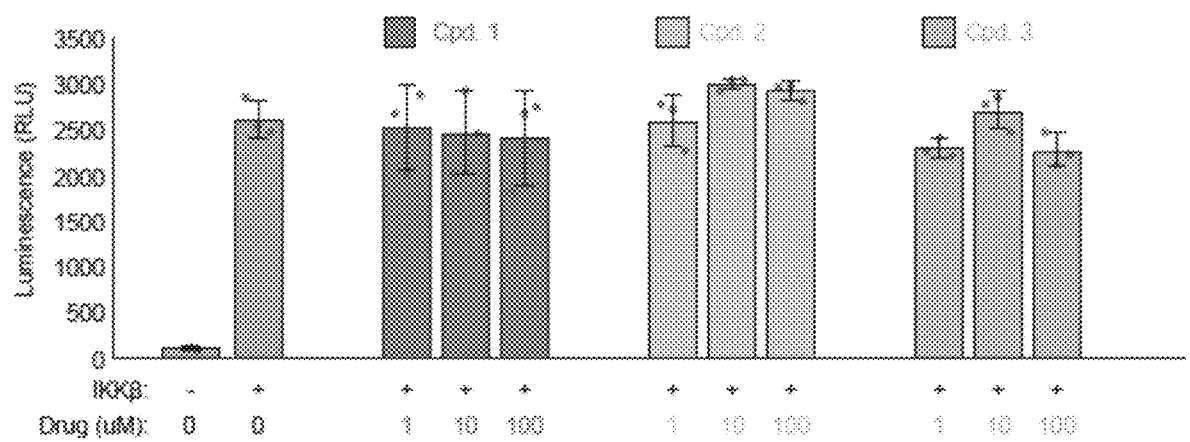
FIG. 17 shows that compounds do not inhibit IKKβ kinase activity. Luminescence-based in vitro kinase reactions using a recombinant activated IKKβ and a substrate peptide derived from human IkBα. For compounds 1 (orange), 2 (tan), and 3 (teal), kinase activity is not inhibited even at 10-fold higher concentrations than used in cell-based experiments. Minus and plus symbols respectively indicate the absence or presence of recombinant kinase in the reaction. Data shown for 3 replicate experiments (indicated by dot plots), ± standard deviation.

Compounds 2 and 3 also showed significant correlations (FIG. 1*b*) with ubiquitination machinery and kinases, including IKK, that are common to basal cellular processes and inflammatory responses (Beck et al., *Endocr. Rev.*, 30:830-882 (2009)). Interleukin-1 (IL1) is one such inflammatory cytokine that activates NF-kB via the functional IKK complex, but independent of interactions between TRADD and TRAF2. Instead, IL1 utilizes TRAF6 which does not share any of the four serines (S453, S454, S455, and S467; FIG. 1a) identified as the binding substrate of the compounds. Consistent with this observation and in contrast with the TNF response, IL1-induced dynamics of nuclear NF-kB were indistinguishable between cells pretreated with compounds 2 or 3 and IL1-only control cells (FIGS. 4 and 15). Furthermore, cytotoxicity analysis and assessment of IKKβ kinase activity in vitro demonstrated that compounds 1, 2 and 3 have low cytotoxicity and no direct inhibitory activity over IKKβ kinase activity at the concentrations used in this study (FIGS. 16 and 17). Together the results demonstrate that the IKK and NF-kB systems are intact in cells exposed to the compounds and suggest that the mode of action for both compounds is directed specifically at the level of the mature TNFR1 complex.

Example 4

Small Molecules Prevent Formation of the Mature TNFR1 Complex

Figure 18:
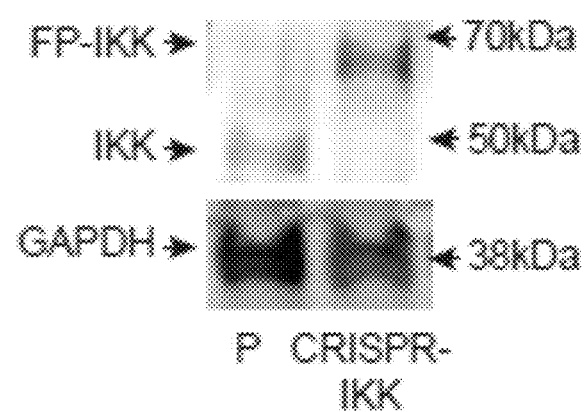
FIG. 18 shows Western blot of IKKγ. Western blot of IKKγ in lysates from parental U2OS cells (P) and U2OS cells that were modified using CRISPR to express EGFP-IKKγ. The molecular weight of the FP-IKKγ band in the CRISPR-modified cell line is shifted upward by 32 kDa, consistent with the expected molecular weight of the EGFP fusion protein. The absence of wild type IKKγ in the CRISPR-modified cell line suggests that both alleles of the IKKγ-encoding gene integrated the EGFP sequence.

Induced proximity between IKK and other regulatory factors within the mature TNFR1 complex is essential for TNF-induced NF-kB activation and may be perturbed in cells exposed to compounds 2 and 3. To test this hypothesis, and directly observe the penultimate recruitment of IKK to the TNFR1 complex, CRISPR/Cas9 was used to target the γ-subunit of IKK (also known as NEMO) for FP fusion and live-cell imaging in U2OS cells (FIG. 18).

Figures 5A, 5B:
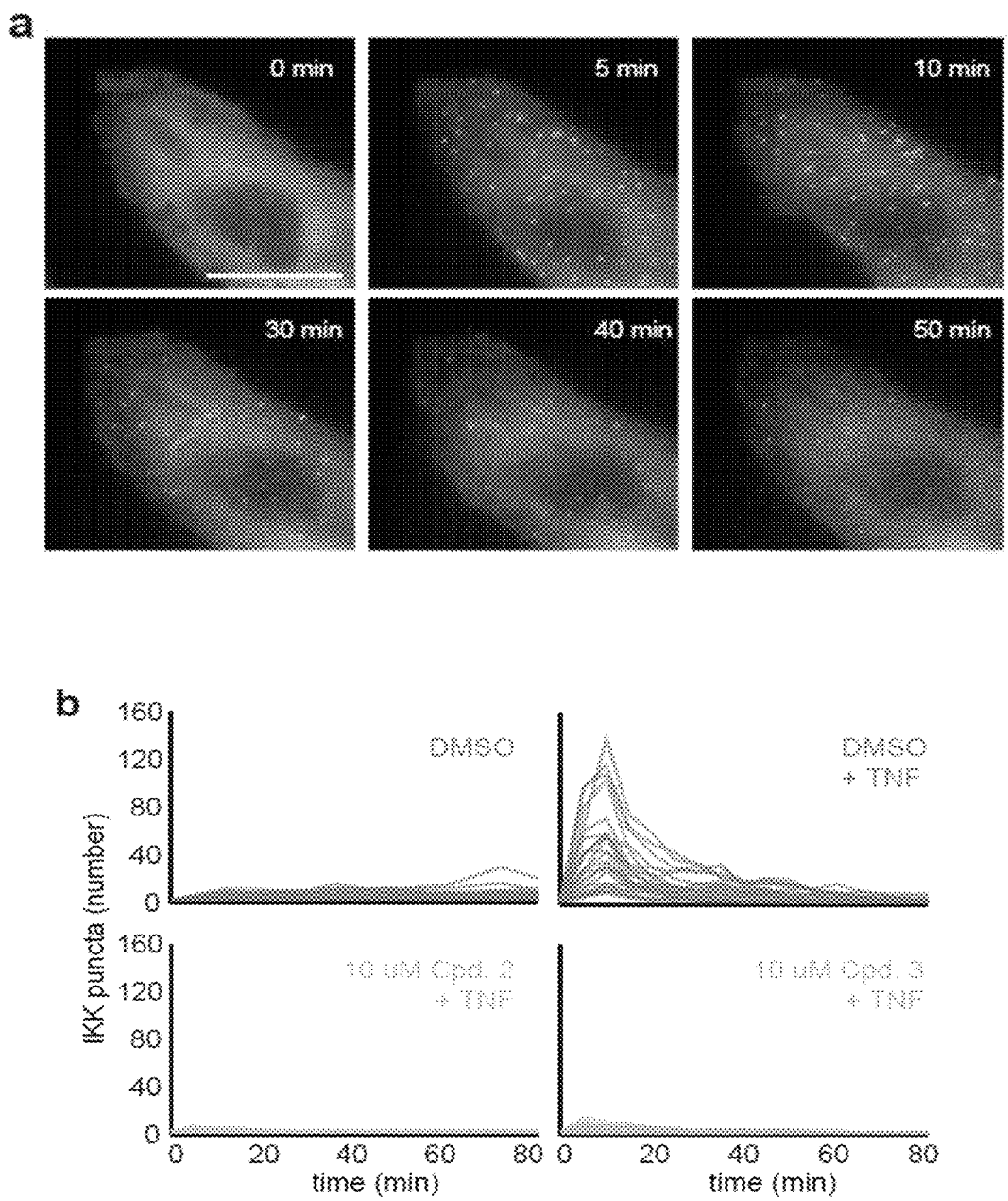
FIGS. 5A-5B shows small molecules disruptors of NF-kB limit the formation of IKKγ puncta in TNF-stimulated cells.

FP-IKK was diffuse within the cytoplasm of unstimulated cells and rapidly localized to punctate structures near the plasma membrane after exposure to TNF (FIG. 5a). Because a key role of the TNFR1 complex is to recruit and activate IKK at ubiquitin scaffolds (Ea et al., *Mol. Cell.*, 22:245-257 (2006)), detection of FP-IKK puncta can be used to measure maturation of the complex in living cells. The number of FP-IKK puncta in single cells peaked at 15 minutes and dissolved within an hour of TNF stimulation (FIG. 5b). Although the recruitment and dissolution dynamics of FP-IKK are prolonged when compared with a previous study that overexpressed a fusion of mouse IKγ in U2OS cells (Tarantino et al., *J. Cell. Biol.*, 204:231-245 (2014)), they are otherwise qualitatively similar.

Figures 19A, 19B:
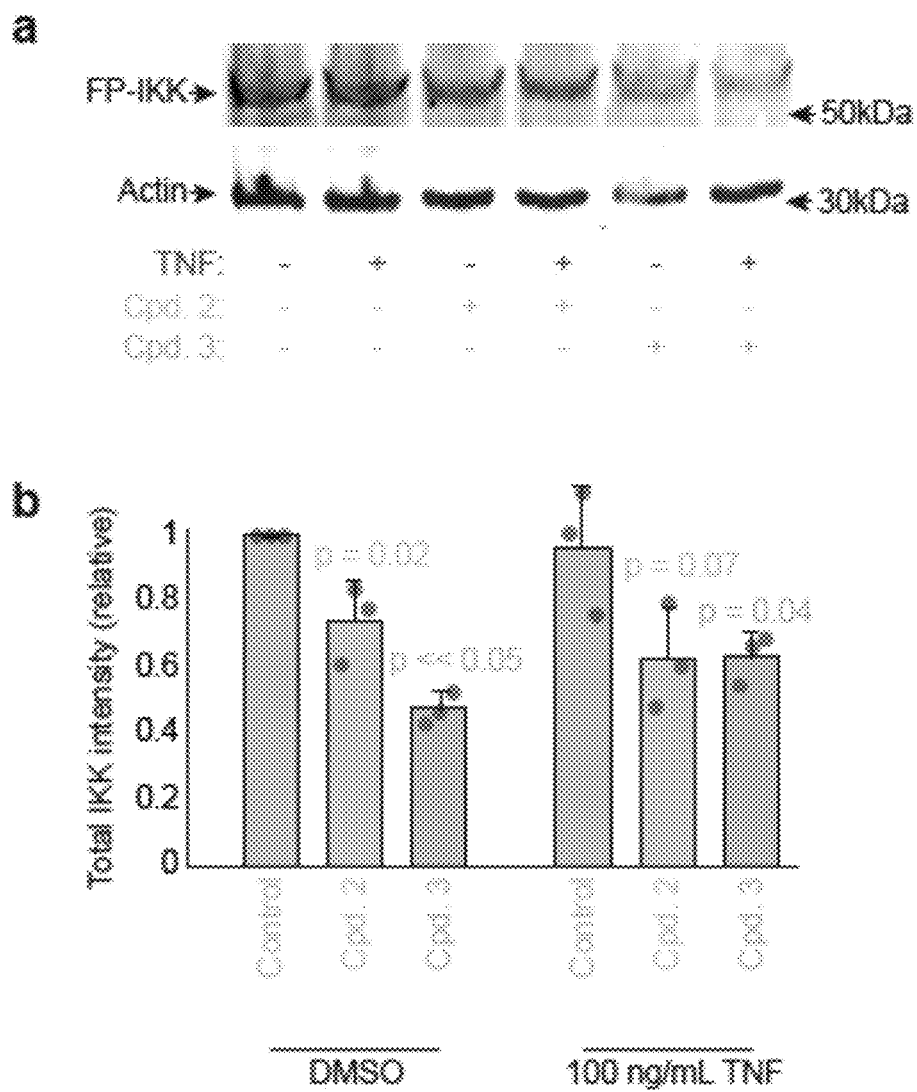
FIGS. 19A-19B shows IKKγ expression in the presence of compounds 2 and 3.

Consistent with observations for NF-kB, the number of TNF-induced puncta were greatly reduced in cells that were pretreated with compounds 2 or 3 before exposure to TNF (FIG. 5b). Unexpectedly, the compounds also reduced the overall expression level of IKKγ (FIG. 19) through an unknown mechanism that may relate to TRAF-dependent ubiquitination cascades that regulate the ambient stability of other NF-kB-inducing kinases (Zarnegar et al., *Nat. Immunol.*, 9:1371-1378 (2008)). Overall, the absence of IKKγ mobilization in TNF-stimulated cells indicate that micromolar concentrations of compounds 2 and 3 prevent a key proximity-induced mechanism provided otherwise through assembly of the mature TNFR1 complex.

Example 5

Analysis of Gene Expression Data

Preparation and analysis of gene expression (GE) data was performed as described previously (Pabon et al., *PLoS Comput. Biol.*, 14 (2018)). Briefly, gene knockdown (KD) and compound treatment GE signatures were extracted from the LINCS L1000 Phase I and Phase II datasets (GEO accession IDs: GSE70138 and GSE92742). Signatures for the 1680 small molecules and 3104 gene KD experiments that had been performed in at least four of the seven most common LINCS cells lines (A549, MCF7, VCAP, HA1E, A375, HCC515, HT19) were collected. For each compound—KD signature pair in the dataset, several cell-specific quantitative features were computed, most importantly:

Direct correlation: the Pearson correlation coefficient between the compound treatment and the gene KD expression signatures in the given cell line, and Indirect correlation: the fraction of the KD protein's interaction partners, as defined by BioGrid (Chatr-Aryamontri, A. et al. *Nucleic Acids Res* 43, D470-478 (2015)), whose respective KD signatures were highly correlated with the compound signature.

Three additional features, quantifying baseline drug activity in the cell and the maximum & average compound-induced differential expression levels of NF-kB pathway proteins (Pabon et al., *PLoS Comput. Biol.*, 14 (2018)), were also calculated and used in subsequent classification.

Using a Random Forest (RF) classifier trained the expression signatures of 152 FDA-approved drugs with known mechanism(s) of action, features for every compound-KD pair (n=5,214,720) were used to predict the probability that the compound would inhibit the KD protein's interaction network. The top-100 predicted interactions for each compound were extracted, and compounds whose predicted targets were enriched in TNF-induced NF-kB signaling genes (n=360) were collected for structural analysis.

Example 6

Structural Analysis

Figure 20:
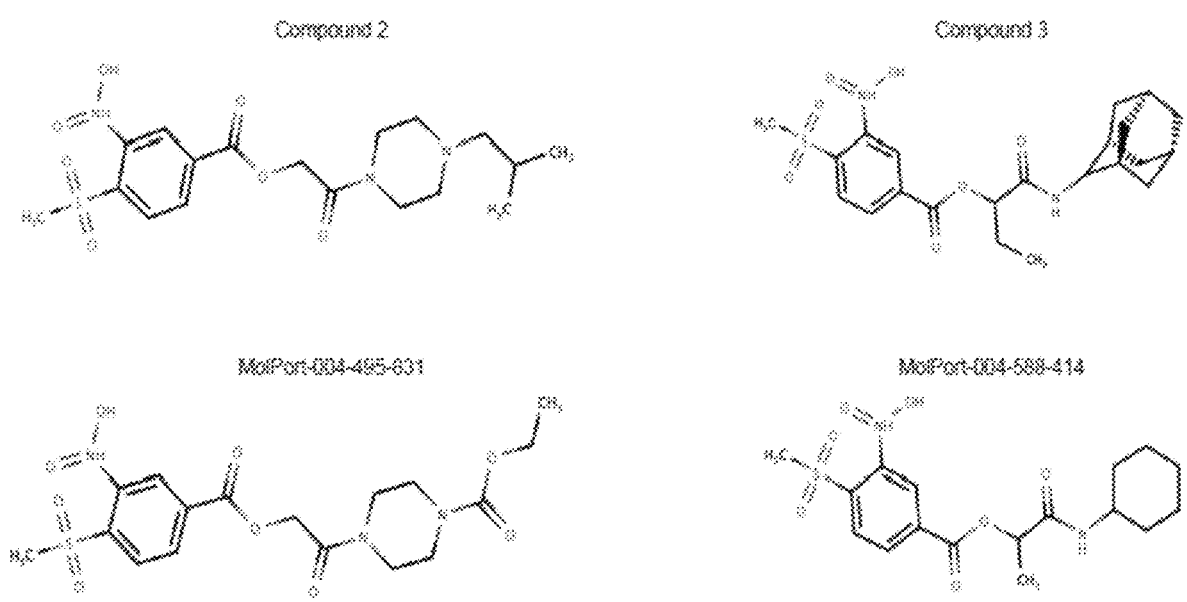
FIG. 20 shows that the chemical structure of compounds 1-isobutylpiperazine group in compound 2 was replaced by ethyl piperazine-1-carboxylate in Molprot-004-495-831. Bulkier adamantan-2-amine in compound 3 was replaced by cyclohexane in Molprot-004-588-414. Note that the modified groups do not participate in any of the key interactions predicted in FIG. 1c, and the changes are almost exclusively on surface/solvent areas.

Structural docking of RF—predicted inhibitors proceeded as previously described (Pabon et al., *PLoS Comput. Biol.*, 14 (2018)). Briefly, representative crystal structures of TNF-inducible NF-kB signaling proteins (FIG. 6) were mined from the PDB (Berman et al., *Nucleic Acids Res.*, 28:235-242 (2000)), optimizing for sequence coverage, structural resolution, and structural diversity. Domain structures were available for all proteins in FIG. 1a with the exception of IKKα. Potential small-molecule binding sites on each protein structure were identified by clustering the output of computational solvent mapping software FTMap (Kozakov et al., *Nature Protocols*, 10:733-755 (2015)). RF-predicted inhibitors were docked to predicted binding sites on each protein structure using smina (Koes et al., *J. Chem. Inf. Model.*, 53:1893-1904 (2013)), and a prospectively validated pipeline (Ye et al., *J. Comput. Aided Mol. Des.*, 30:695-706 (2016); Baumgartner, M. P. & Camacho, C. J., *J. Chem. Inf. Model.*, 56:1004-1012 (2016)). Generic versions of the three promising candidate inhibitors of TRAF2, which showed both biophysical complementarity and broad spectrum transcriptomic correlations with knockdowns in the pathway, were purchased from MolPort for experimental validation. Molport IDs MolPort-000-763-757, MolPort-004-495-831, MolPort-004-588-414 for compounds 1, 2, 3 respectively. Molport versions of compounds 2 and 3 had minor modifications (see FIG. 20) that did not alter their predicted binding profiles.

Example 7

Thermal Shift Assay and Analysis

TRAF2—compound interactions were measured by fluorescence-based thermal shift using an Applied Biosystems ABI QuantStudio(TM) 6 Flex System. All assay experiments used 1 uM GST-TRAF2 (Rockland) per well and 2 X Sybro Orange (Invitrogen) in a buffer containing 50 mM HEPES, pH 7.5, 150 Mm NaCl in a total reaction volume of 15 ul in 384 well plates. Compounds were diluted with DMSO, and each reaction had a final DMSO concentration of 1.5%. PCR plates were covered with optical seal, shaken, and centrifuged after protein and compounds were added. The instrument was programmed in the Melt Curve mode and the Standard speed run. The reporter was selected as Rox and None for the quencher. Each melt curve was programmed as follows: 25° C. for 2 min, followed by a 0.05° C. increase per second from 25° C. to 99° C., and finally 99° C. for 2min. Fluorescence intensity was collected continuously. In the Melt Curve Filter section, X4 (580 ±10)-M4 (623±14) was selected for the Excitation Filter-Emission Filter. The raw data was extracted in MS-Excel format. Each melt curve was normalized between 0 and 1 and the midpoint of the curve was used to determine the melting temperature.

Example 8

Establishing EGFP-RELA/IKKγ CRISPR Knock-in Cells

Construction of Repair Templates for EGFP-IKKγ CRISPR Knock-in: The RelA repair template consisted of DNA sequences for a left homology arm (LHA −544bp, chromosome 11_65663376-chromosome 11_65662383) followed by an EGFP coding sequence with a start codon but no stop codon and a sequence encoding 3x GGSG linker (SEQ ID NO: 1) followed by a right homology arm (RHA +557bp, chromosome 11_65662829-chromosome 11_65662276) were assembled from plasmids synthesized by GeneArt. Synonymous mutations that are not recognized guide RNAs were introduced to prevent interaction the repair template and Cas9. IKBKG DNA sequences for left homology arm (LHA −861bp, chromosome X 154551142-chromosome X 154552002) and right homology arm (RHA +797bp, chromosome X_154552006-chromosome X 154552798) were amplified from Hela genomic DNA using the following primer pairs: IKBKG_LHA_F: 5'GGG CGA ATT GGG CCC GAC GTC GTT TCA CCG TGT TAG CCA GG3' (SEQ ID NO: 2), IKBKG_LHA_R: 5' CAC ATC CTT ACC CAG CAG A3' (SEQ ID NO: 3); IKBKG_RHA_F: 5'AGA GTC TCC TCT GGG GAA GC3 (SEQ ID NO: 4), IKBKG_RHA_R: 5'CCG CCA TGG CGG CCG GGA GCA TGC GAC GTC AGT CTA GGA AAG AAC TCC CCA GTC3' (SEQ ID NO: 5). To generate the fragment containing EGFP overlapping with LHA and RHA, the sequence was synthesized from GeneArt, then amplified the sequence containing EGFP with the primer pairs: IKBKG_EGFP_F 5' TCT GCT GGG TAA GGA TGT G3' (SEQ ID NO: 6), IKBKG_EGFP_R 5' GCT CTT GAT TCT CCT CCA GGC AG 3' (SEQ ID NO: 7). After PCR products were purified, the fragments LHA, RHA, EGFP were cloned to pMK plasmid that was digested with AatII by gibson assembly from NEB.

Construction of Guide RNA: The guide RNAs were designed by the CRISPR Design Tool. Oligonucleotide pairs Rel A sg1 (top): 5'-CACCGCTCGTCTGTAGTGCACGCCG-3' (SEQ ID NO: 8), Rel A sg1 (bottom): 5'-AAACCGGCGTGCACTA-CAGACGAGC-3' (SEQ ID NO: 9); RELA Sg2 (top) 5'-CACCGAGAGGCGGAAATGCGCCGCC-3' (SEQ ID NO: 10), RELA Sg2 (bottom) 5'-AAACCGCGGCGCAT-TTCCGCCTCTC-3' (SEQ ID NO: 11); IKBKG Sg1 (top) 5'-CACCGGCAGCAGATCAGGACGTAC-3' (SEQ ID NO: 12), IKBKG Sg1 (bottom) 5'-AAACGTACGTCCT-GATCTGCTGCC-3' (SEQ ID NO: 13); and IKBKG Sg2 (top) 5'-CACCGCTGCACCATCTCACACAGT-3' (SEQ ID NO: 14), IKBKG Sg2 (bottom) 5'-AAACACTGTGT-GAGATGGTGCAGC-3' (SEQ ID NO: 15) were cloned into the vector pSpCas9n (BB)-2A-Puro (PX462) (Addgene). The pSpCas9n (BB)-2A-Puro-IKKγ_gRNAs vector encoded the guide RNA and the Cas9 nuclease with D10A nickase mutant.

Transfection and Clone Isolation: U2OS cells (2×105 cells per well) were seeded in 6-well plates in complete growth medium. The following day, with pSpCas9n (BB)-2A-Puro-RELA/IKKγ_gRNAs and repair template donor plasmids were linearized using BGLII, and cells were transfected using FuGENE HD (Promega) with a transfection reagent to DNA ratio of 3.5 to 1 and a total DNA amount of 4 μg. After two weeks, cells were subjected to single cell sorting into 96-well plates using Beckman Coulter MoFlo Astrios High Speed. Cells underwent clonal isolation and a positive clone was identified via western blot and confirmed by live-cell imaging.

Example 9

Western Blot Analysis

U2OS cells (parental and expressing EGFP-RelA/IKKγ via CRISPR Knock-in) were cultured for 24 hrs in complete growth medium. After treatments, cells were lysed in SDS-based lysis buffer consisting of 120 mM Tris-Cl, pH 6.8, 4% SDS supplemented with protease and phosphatase inhibitors at 4° C. for 30 min. Protein extracts were clarified by centrifugation at 4° C. at 12,000×g for 10 min. Lysate protein levels were quantified by BCA assay (Pierce). Samples were separated by SDS-PAGE, 25 μg total protein per lane, then transferred to PVDF membranes. Blocking was done in 5% milk in TBS for 1 hour. Primary antibodies directed at RelA and β-actin (#4764 and #3700 respectively; Cell Signaling Technology), IKKγ and GAPDH (sc-8330 and sc25778 respectively; Santa Cruz) were diluted in 5% milk in TBS-T and incubated overnight at 4° C. Alexa 680/800-conjugated secondary antibodies (LICOR) were used in combination with an Odyssey (LI-COR) scanner for detection and quantification of band intensities.

Example 10

Live-Cell Imaging and Analysis

Live cells were imaged in an environmentally controlled chamber (37° C., 5% CO$_2$) on a DeltaVision Elite microscope equipped with a pco.edge sCMOS camera and an Insight solid-state illumination module (GE). U2OS cells expressing FP-RelA/IKKγ were seeded at a density of 25000 cells/well 24 hours prior to live-cell imaging experiments on no. 1.5 glass bottom 96 well imaging plates (Matriplate). For imaging of FP-RelA nuclear translocation, live-cells were pre-treated with DMSO or indicated concentrations of compounds for 2 hours before exposure to either 100 ng/ml recombinant human TNF (Peprotech) or 100 ng/ml recombinant human IL1β (Peprotech). Wide-field epifluorescence and DIC images were collected using a 20× LUCPLFLN objective (0.45NA; Olympus). Cells were imaged for at least 30 minutes prior to addition of compounds. For detection of IKKγ puncta, live-cells were pre-treated with DMSO or indicated concentration of compounds for 2 hours before exposure to 100 ng/ml TNF. Wide-field epifluorescence and DIC images were collected using a 60× LUCPLFLN objective. For all treatments, cytokine mixtures were prepared and pre-warmed so that addition of 120 uL added to wells results in a final concentration as indicated. Time-lapse images were collected over at least 4 fields per condition with a temporal resolution of 5 minutes per frame. Quantification of nuclear FP-RelA localization and the formation IKKγ puncta from flat-field and background corrected images was performed using customized scripts in Matlab and ImageJ.

Example 11

Fixed-Cell Immunofluorescence and Analysis

For fixed-cell measurement of endogenous RelA (FIG. 10), U2OS cells were seeded into plastic bottom 96 well imaging plates (Fisher) at 6000 cell/well 24 hours prior to treatment. On the day of the experiment, media containing TNF was prepared at 15× the desired concentration for each well. Timing of TNF treatment was planned so fixation (0, 10, 30, 60, 90, 120 minutes) occurred simultaneously for all time points at the same time. Pre-warmed 15× cytokine mixture was spiked into wells and mixed. Between treatments the cells remained in environmentally controlled conditions (37° C. and 5% $CO_2$).

At time zero, media was removed from the wells, 185 μL of PBS was used to wash the wells, and wells were incubated at room temp in 120 μL of 4% paraformaldehyde (PFA) in 1× PBS for 10 minutes. Wells were then washed 3× three minutes with 185 μL 1× PBS and then incubated in 120 μL 100% methanol for 10 min at room temp. Next wells were washed 3× three minutes in PBS-T (1×PBS 0.1% Tween 20) followed by 120 μL of primary antibody solution (3% BSA PBS-T, 1 μg/mL NF-κB p65 F-6 (sc-8008; Santa Cruz)). Plates were wrapped in para-film and left to incubate at 4° C. overnight. The following morning, wells were washed 3× five minutes in 185 μL PBS-T followed by incubation for 1 hour in 120 μL of the secondary antibody solution (3% BSA PBS-T, 4 μg/mL Goat anti-Mouse IgG Alexa Fluor 647 (Thermo Fisher)). 185 μL PBS-T was used to wash the wells for 5 minutes and they were put into 120 ul Hoechst solution (PBS-T, 200 ng/mL Hoechst) for 20 min. Finally, wells were washed five minutes with PBST and then 185 μL PBS was used to fill the wells and keep the cells hydrated during imaging. Cells were imaged using Delta Vision Elite imaging system at 20× magnification with a LUCPLFLN objective (0.45NA; Olympus). Analysis was done using Cell Profiler to segment cells and quantify median nuclear intensity values. Further analysis was performed using custom scripts in MATLAB.

Example 12

Permutation Tests to Assess Statistical Significance between Descriptors

For permutation tests, data from the TNF-only and the indicated experimental condition were combined and randomly distributed into 'Permuted control' and 'Permuted experimental' bins without replacement, preserving the size of the original control and experimental data sets. $10^6$ permutations were performed and the difference between the means of permuted control and experimental data were calculated for each condition to generate a histogram. Two-tailed p-values were determined by computing the fraction of permuted data sets where $\Delta\text{mean}_{permuted} \geq \Delta\text{mean}_{unpermuted}$ (FIGS. 12, 13, and 15).

Example 13

In Vitro IKKβ Kinase Assay

Recombinant activated IKKβ and the IKKtide substrate (Promega, V4502) with the ADP-Glo bioluminescence assay (Promega, V7001) was used to evaluate the effects of compounds 1, 2 and 3 on IKKβ kinase activity. 1× kinase buffer A (40 mM Tris-HCl pH 7.4, 20 mM $MgCl_2$, 0.1 mg/mL BSA, supplemented with 2 mM $MnCl_2$, 2 mM DTT and 100 μM Sodium vanadate) was used to prepare all components of the reaction. All components were prepared in a 96-well plate and transferred to every other well of a 384-well opaque plate (Sigma-Aldrich, CLS3825-10EA) using a multichannel pipet. A 2.5× ATP/IKKtide substrate mix (62.5 μM ATP mixed with 0.5 μg/μL IKKtide) was prepared, and a 5× concentration of the indicated concentration of compounds in 0.5% DMSO, maintaining a final DMSO concentration of 0.1% in all reactions. The components of this kinase reaction were added to each well in the following order: 1 μL of 5× compound or buffer only, 2 μL of 100 ng/μL of IKKβ Kinase or buffer, and 2 μL of 2.5× ATP/IKKtide substrate mix. The plate was briefly spun, and the reaction incubated at room temperature for 1 h. Next, 5 μL of ADP-Glo reagent were added to each well, spun and incubated for 40 minutes at room temperature. Finally, 10 μL of Kinase Detection Reagent were added to each well and incubated for 30 minutes at room temperature. Luminescence from each well was measured using an integration time of 500 ms in a M4 microplate reader (SpectraMax). Data from triplicate reactions were extracted and plotted.

Example 14

Compound Toxicity Comparison

Cytotoxicity of the three compounds was compared with Bay 11-7082 (Cayman, 10010266), an inhibitor of the NF-κB pathway at working concentrations of 1-10 μM, using the LIVE/DEAD Cell Imaging Kit (488/570) (Invitrogen, R37601). For each condition, 15,000 U2OS cells were seeded in 200 μL of growth medium in each well of 96-well plate 48 h before microscopy. Next, medium was changed to medium containing either DMSO, 10 μM of indicated compound, or 10 μM of Bay 11-7082 for the indicated duration (2 h, 16 h, or 24 h). Before imaging, medium was changed to phenol red-free FluoBrite DMEM (Gibco, A18967-01) containing 300 ng/mL of Hoechst 33342, and 1:10000 of both Live Green and Dead Red dyes of the LIVE/DEAD Cell Imaging Kit. Cells were incubated for 60 minutes and imaged on the Delta Vision Elite imaging system at 20× magnification with a LUCPLFLN objective (0.45NA; Olympus). Analysis was done using Cell Profiler to segment cells and quantify median nuclear intensity values. Further analysis was performed using custom scripts in MATLAB. Data from biological triplicates were plotted as the mean ± SD.

It will be apparent to those skilled in the art that various modifications and variations can be made in the methods and compositions of the present invention without departing from the spirit or scope of the invention. Thus, it is intended that the present invention cover the modifications and variations of this invention, provided they come within the scope of the appended claims and their equivalents.

What is claims is:

1. A compound represented by formula (I):

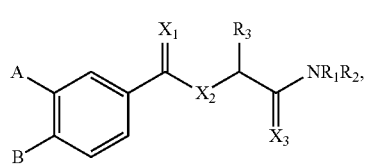

or a salt or hydrate thereof, wherein:

A is an azinic acid;

B is an alkyl sulfonyl;

$X_1$ and $X_3$ are independently selected from O, NOH, NO-alkyl, and $C(CN)_2$;

$X_2$ is selected from O, NH, and NF;

$R_1$ is H or alkyl and $R_2$ is an optionally substituted alkyl or cycloalkyl, or $R_1$ and $R_2$ together form an optionally substituted 5- or 6-membered heterocycle; and $R_3$ is selected from H, F, and an optionally substituted alkyl, where the compound of formula (I) is not:

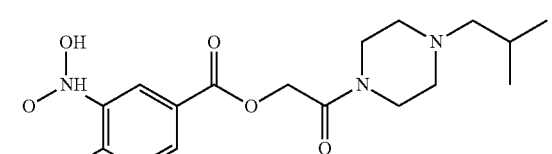

or

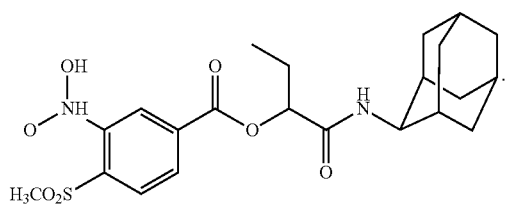

2. The compound of claim 1, wherein -NRiR2 is represented by:

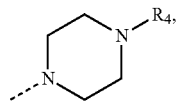

wherein $R_4$ is an optionally substituted alkyl, alkene, alkyne, or —$COOR_5$, where $R_5$ is an optionally substituted alkyl or cycloalkyl.

3. The compound of claim 1, wherein $X_1$, $X_2$ and $X_3$ are O.

4. The compound of claim 1, wherein $R_3$ is H.

5. The compound of claim 1, wherein $R_2$ is a cyclopentyl or cyclohexyl.

6. A pharmaceutical composition comprising the compound of claim 1 and at least one pharmaceutically acceptable carrier.

7. The pharmaceutical composition of claim 6, wherein the composition is suitable for administration to a human.

8. The pharmaceutical composition of claim 6, formulated into a dosage form:
   (a) selected from the group consisting of liquid dispersions, gels, aerosols, lyophilized formulations, tablets, and capsules;
   (b) selected from the group consisting of controlled release formulations, fast melt formulations, delayed release formulations, extended release formulations, pulsatile release formulations, and mixed immediate release and controlled release formulations; or (c) any combination of (a) and (b).

9. The pharmaceutical composition of claim 6, formulated for administration selected from the group consisting of oral, pulmonary, rectal, colonic, parenteral, intracisternal, intravaginal, intraperitoneal, intravenous, subcutaneous, intramuscular, nebulization, inhalation, ocular, otic, local, buccal, nasal, and topical administration.

10. A method of preventing formation of mature TNFR1 complex, comprising contacting a cell with a compound of formula (I):

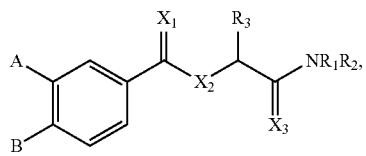

or a salt or hydrate thereof, wherein:
A is an azinic acid;
B is an alkyl sulfonyl;
$X_1$ and $X_3$ are independently selected from O, NOH, NO-alkyl, $CF_3$, and $C(CN)_2$;
$X_2$ is selected from O, NH, and NF;
$R_1$ is H or alkyl and $R_2$ is an optionally substituted alkyl or cycloalkyl, or $R_1$ and $R_2$ together form an optionally substituted 5- or 6-membered heterocycle.

11. The method of claim 10, wherein the cell is a human cell.

12. The method of claim 10, wherein the method is in vivo or in vitro.

13. The method of claim 12, wherein the contacting is in vivo in a subject suffering from a disease caused by blockade of TNF-induced signaling or in a subject suffering from a disease caused by inflammation-associated cancers that are potentiated by TNF-induces NFkB signaling.

14. The method of claim 13, wherein:
   (a) the disease is selected from the group consisting of rheumatoid arthritis, ankylosing spondylitis, inflammatory bowel disease, and psoriasis; or
   (b) the cancer is selected from the group consisting of aggressive diffuse large B-cell lymphoma, metastatic carcinomas, tumors of the colon, tumors of the lung, tumors of the pancreas, and tumors of the brain.

15. A method of inhibiting a TNF-induced nuclear factor kB (NF-kB) inflammation pathway, comprising contacting a cell with a compound of formula (I):

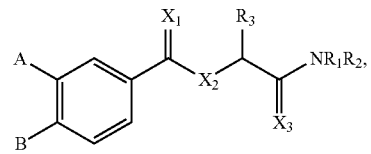

or a salt or hydrate thereof, wherein:
A is an azinic acid;
B is an alkyl sulfonyl;
$X_1$ and $X_3$ are independently selected from O, NOH, NO-alkyl, $CF_3$, and $C(CN)_2$;
$X_2$ is selected from O, NH, and NF;
$R_1$ is H or alkyl and $R_2$ is an optionally substituted alkyl or cycloalkyl, or $R_1$ and $R_2$ together form an optionally substituted 5- or 6-membered heterocycle.

16. The method of claim 15, wherein the cell is a human cell.

17. The method of claim 15, wherein the method is in vivo or in vitro.

18. The method of claim 17, wherein the contacting is in vivo in a subject suffering from a disease caused by blockade of TNF-induced signaling or in a subject suffering from a disease caused by inflammation-associated cancers that are potentiated by TNF-induced NFkB signaling.

19. The method of claim 18, wherein:
   (a) the disease is selected from the group consisting of rheumatoid arthritis, ankylosing spondylitis, inflammatory bowel disease, and psoriasis; or (b) the cancer is selected from the group consisting of aggressive diffuse large B-cell lymphoma, metastatic carcinomas, tumors of the colon, tumors of the lung, tumors of the pancreas, and tumors of the brain.

20. A method of treating a subject suffering from a disease caused by blockade of TNF-induced signaling, comprising administering to the subject in need thereof a pharmaceutically effective amount of the compound of claim 1.

21. The method of claim 20, wherein the disease caused by blockade of TNF-induced signaling is selected from the group consisting of rheumatoid arthritis, ankylosing spondylitis, inflammatory bowel disease, and psoriasis.

* * * * *